(12) United States Patent
Ye et al.

(10) Patent No.: US 8,652,820 B2
(45) Date of Patent: Feb. 18, 2014

(54) **THERMOTOLERANT NON-K12 *ESCHERICHIA COLI* PHYTASE AND ITS PRODUCTION**

(75) Inventors: Xiuyun Ye, FuZhou (CN); Renkuan Li, FuZhou (CN); Weigang Jin, FuZhou (CN); Caifang Chen, FuZhou (CN)

(73) Assignee: Fujian Fuda Biotech Co. Ltd., FuZhou (CN)

(*) Notice: Subject to any disclaimer, the term of this patent is extended or adjusted under 35 U.S.C. 154(b) by 289 days.

(21) Appl. No.: 13/128,566

(22) PCT Filed: Nov. 14, 2008

(86) PCT No.: PCT/CN2008/073050
§ 371 (c)(1),
(2), (4) Date: May 10, 2011

(87) PCT Pub. No.: WO2010/054513
PCT Pub. Date: May 20, 2010

(65) Prior Publication Data
US 2012/0021488 A1 Jan. 26, 2012

(51) Int. Cl.
| | | |
|---|---|---|
| *C12N 9/16* | (2006.01) |
| *C12Q 1/68* | (2006.01) |
| *C12P 21/06* | (2006.01) |
| *C12P 21/04* | (2006.01) |
| *C12N 15/00* | (2006.01) |
| *C07H 21/04* | (2006.01) |

(52) U.S. Cl.
USPC .......... 435/196; 435/6.1; 435/69.1; 435/71.1; 435/252.3; 435/320.1; 536/23.2

(58) Field of Classification Search
None
See application file for complete search history.

(56) References Cited

U.S. PATENT DOCUMENTS

| 4,824,786 | A | | 4/1989 | Hanson et al. |
| 5,436,156 | A | | 7/1995 | Van Gorcom et al. |
| 5,565,350 | A | | 10/1996 | Kmiec |
| 6,855,365 | B2 | | 2/2005 | Short et al. |
| 2004/0091968 | A1 | * | 5/2004 | Short et al. ................... 435/69.1 |

FOREIGN PATENT DOCUMENTS

| CN | 1592791 | 3/2005 |
| CN | 1622824 | 6/2005 |
| CN | 101260391 | 9/2008 |
| EP | 0296484 | 12/1988 |
| WO | 93/22443 | 11/1993 |
| WO | 2004/037998 | 5/2004 |
| WO | 2006/063588 | 6/2006 |

OTHER PUBLICATIONS

Branden et al. Introduction to Protein Structure, Garland Publishing Inc., New York, p. 247, 1991.*
Dassa et al. The complete nucleotide sequence of the *Escherichia coli* gene appA reveals significant homology between pH 2.5 acid phosphatase and glucose-1-phosphatase. J Bacteriol. Sep. 1990;172(9):5497-500.*
Jia et al. Purification, crystallization and preliminary X-ray analysis of the *Escherichia coli* phytase. Acta Crystallogr D Biol Crystallogr. Jul. 1, 1998;54(Pt 4):647-9.*
Supplementary, European Search report issued Oct. 30, 2012 in corresponding European patent application, 7 pages total.
Chang et al., "Codon optimization of candida rugosa lip1 gene for improving expression in *Pichia pastoris* and biochemical characterization of the purified recombinant LIP1 lipase," Journal of Agricultural and Food Chemistry, 2006, vol. 54, No. 3, pp. 815-822.
Nagata et al., "Growth of *Escherichia coli* ATCC 9637 through the uptake of compatible solutes at high osmolarity," Journal of Bioscience and Bioengineering, 2001, vol. 92, No. 4, pp. 324-329.
International Search Report of PCT/CN2008/073050, mailed Aug. 13, 2009.
Mroz et al., "Apparent Digestibility and Retention of Nutrients Bound to Phytate Complexes as Influenced by Microbial Phytase and Feeding Regimen in Pigs," Journal of Animal Science, 1994, vol. 72, pp. 126-132.
Kornegay et al., "Response of broilers to graded levels of microbial phytase added to maize-soyabean-meal-based diets containing three levels of non-phytate phosphorus," British Journal of Nutrition, 1996, vol. 75, pp. 839-852.
Rao et al., "Enhancement of phytate phosphorus availability in the diets of commercial broilers and layers," Animal Feed Science and Technology, 1999, vol. 79, pp. 211-222.
Ravindran et al., "Influence of Microbial Phytase on Apparent Ileal Amino Acid Digestibility of Feedstuffs for Broilers," Poultry Science, 1999, vol. 78, pp. 699-706.
Altschul et al., "Basic Local Alignment Search Tool," J. Mol. Biol., 1990, vol. 215, pp. 403-410.
Dnastar, Inc., "Sequence Alignment in Lasergene: An Overview," http://www.dnastart.com, May 30, 2002.
Pearson, "Searching Protein Sequence Databases—Is Optimal Best?", Computation Methods in Genome Research, 1994, pp. 111-120.

(Continued)

*Primary Examiner* — Yong Pak
(74) *Attorney, Agent, or Firm* — Hamre, Schumann, Mueller & Larson, P.C.

(57) ABSTRACT

This invention relates to cloning and sequencing of thermotolerant phytase gene from Non-K12 *Escherichia coli* strain, ATCC 9637, phytase gene expression in *Escherichia coli* expression system, codon usage optimized and expression in *Pichia pastoris, Pichia methanolica* and *Kluyeromyces lactis*. The high level yield and thermotolerant enzyme was produced from fermentation of *Pichia pastoris* with optimized codon of phytase gene.

11 Claims, 13 Drawing Sheets

(56) References Cited

OTHER PUBLICATIONS

Bailey et al,, "Fitting a mixture model by expectation maximization to discover motifs in biopolymers," Proceedings of the Second International Conference on Intelligent Systems for Molecular Biology, 1994, pp. 28-36.

Bailey et al., "Combining evidence using p-values: application to sequence homology searches," Bioinformatics, 1998, vol. 14, No. 1, pp. 48-54.

Needleman et al., "A General Method Applicable to the Search for Similarities in the Amino Acid Sequence of Two Proteins," J. Mol. Biol. 1970, vol. 48, pp. 443-453.

Springer et al., "Sequence and characterization of mxaB, a response regulator involved in regulation of methanol oxidation, and of mxaW, a methanol-regulated gene in *Methylobacterium extorquens* AM1," FEMS Michrobiology Letters, 1998, vol. 160, pp. 119-124.

Follner et al., "Expression of polyhydroxyalkanoic-acid-biosynthesis genes in methylotrophic bacteria relying on the ribulose monophosphate pathway," Appl Microbiol Biotechnol, 1993, vol. 40, pp. 284-291.

Ueda et al., "Transformation of a Methylotrophic Bacterium, *Methylobacterium extorquens*, with a Broad-Host-Range Plasmid by Electroporation," Applied and Environmental Microbiology, 1991, vol. 57, No. 4, pp. 924-926.

Hamilton et al., "New Method for Generating Deletions and Gene Replacements in *Escherichia coli*," Journal of Bacteriology, 1989, vol. 171, No. 9, pp. 4617-4622.

Balbas et al., "Plasmid pBRINT: a vector for chromosomal insertion of cloned DNA," Gene, 1993, vol. 136, pp. 211-213.

Guldener et al., "A new efficient gene disruption cassette for repeated use in budding yeast," Nucleic Acids Research, 1996, vol. 24, No. 13, pp. 2519-2524.

Smith et al., "PCR-based gene disruption in *Saccharomyces cerevisiae*," Methods in Molecular and Cellular Biology, 1995, vol. 5, pp. 270-277.

Deshpande, "Ethanol Production from Cellulose by Coupled Saccharification/Fermentation using *Saccharomyces cerevisiae* and Cellulase Complex from *Sclerotium rolfsii* UV-8 Mutant," Applied Biochemistry and Biotechnology, 1992, vol. 36, pp. 227-234.

Chen et al., "Separation of phytic acid and other related inositol phosphates by high-performance ion chromatography and its applications," Journal of Chromatography A, 2003, vol. 1018, pp. 41-52.

Scorer et al., "Rapid selection using G418 of high copy number transformants of *Pichia pastoris* for high-level foreign gene expression," Bio/Technology, 1994, vol. 12, pp. 181-184.

Lowry et al., "Protein measurement with the folin phenol reagent," J. Biol. Chem. 193 (1951) 265-275.

GB/T 18634-2009 "Determination of feed phytase activity—Spectrophotometric method" issued Jul. 1, 2002 with (7 pages total, English language abstract).

Zou, "Study On The Determination Condition of Phytase Activity By Molybdenum Yellow and Molybdenum Blue Method," China Feed, 2005, issue 3, pp. 37-39 (English language abstract provided).

* cited by examiner

FIG. 1A

```
    ATGAAAGCGATCTTAATCCCATTTTTATCTCTTCTGATTCCGTTAACCCCGCAATCTGCA
1   ------------+---------+---------+---------+---------+---------+ 60
    TACTTTCGCTAGAATTAGGGTAAAAATAGAGAAGACTAAGGCAATTGGGGCGTTAGACGT
    M  K  A  I  L  I  P  F  L  S  L  L  I  P  L  T  P  Q  S  A   -

TTCGCTCAGAGTGAGCCGGAGCTGAAGCTGGAAAGTGTGGTGATTGTCAGTCGTCATGGT
61  ------------+---------+---------+---------+---------+---------+ 120
    AAGCGAGTCTCACTCGGCCTCGACTTCGACCTTTCACACCACTAACAGTCAGCAGTACCA
    F  A  Q  S  E  P  E  L  K  L  E  S  V  V  I  V  S  R  H  G   -

GTGCGTGCTCCAACCAAGGCCACGCAACTGATGCAGGGTGTCACCCCAGACGCATGGCCA
121 ------------+---------+---------+---------+---------+---------+ 180
    CACGCACGAGGTTGGTTCCGGTGCGTTGACTACGTCCCACAGTGGGGTCTGCGTACCGGT
    V  R  A  P  T  K  A  T  Q  L  M  Q  G  V  T  P  D  A  W  P   -

ACCTGGCCGGTAAAACTGGGTTGGCTGACACCGCGCGGTGGTGAGCTAATCGCCTATCTC
181 ------------+---------+---------+---------+---------+---------+ 240
    TGGACCGGCCATTTTGACCCAACCGACTGTGGCGCGCCACCACTCGATTAGCGGATAGAG
    T  W  P  V  K  L  G  W  L  T  P  R  G  G  E  L  I  A  Y  L   -

GGACATTACCAACGCCAGCGTCTGGTAGCCGACGGATTGCTGGCGAAAAAGGGCTGCCCG
241 ------------+---------+---------+---------+---------+---------+ 300
    CCTGTAATGGTTGCGGTCGCAGACCATCGGCTGCCTAACGACCGCTTTTTCCCGACGGGC
    G  H  Y  Q  R  Q  R  L  V  A  D  G  L  L  A  K  K  G  C  P   -

CAGTCTGGTCAGGTCGCGATTATTGCTGATGTCGACGAGCGTACCCGTAAAACAGGCGAA
301 ------------+---------+---------+---------+---------+---------+ 360
    GTCAGACCAGTCCAGCGCTAATAACGACTACAGCTGCTCGCATGGGCATTTTGTCCGCTT
    Q  S  G  Q  V  A  I  I  A  D  V  D  E  R  T  R  K  T  G  E   -

GCCTTCGCCGCCGGGCTGGCACCTGACTGTGCAATAACCGTACATACCCAGGCAGATACG
361 ------------+---------+---------+---------+---------+---------+ 420
    CGGAAGCGGCGGCCCGACCGTGGACTGACACGTTATTGGCATGTATGGGTCCGTCTATGC
    A  F  A  A  G  L  A  P  D  C  A  I  T  V  H  T  Q  A  D  T   -

TCCAGTCCCGATCCGTTATTTAATCCTCTAAAAACTGGCGTTTGCCAACTGGATAACTCG
421 ------------+---------+---------+---------+---------+---------+ 480
    AGGTCAGGGCTAGGCAATAAATTAGGAGATTTTTGACCGCAAACGGTTGACCTATTGAGC
    S  S  P  D  P  L  F  N  P  L  K  T  G  V  C  Q  L  D  N  S   -

AACGTGACTGACGCGATCCTCAGCAGGGCAGGAGGGTCAATTGCTGGCTTTACCGGGCAT
481 ------------+---------+---------+---------+---------+---------+ 540
    TTGCACTGACTGCGCTAGGAGTCGTCCCGTCCTCCCAGTTAACGACCGAAATGGCCCGTA
    N  V  T  D  A  I  L  S  R  A  G  G  S  I  A  G  F  T  G  H   -

CGGCAAACGGCGTTTCGCGAACTGGAACGGGTGCTTAATTTTCCGCAATCAAACTTGTGC
541 ------------+---------+---------+---------+---------+---------+ 600
    GCCGTTTGCCGCAAAGCGCTTGACCTTGCCCACGAATTAAAAGGCGTTAGTTTGAACACG
    R  Q  T  A  F  R  E  L  E  R  V  L  N  F  P  Q  S  N  L  C   -

CTTAAACGTGAGAAACAGGACGAAAGCTGTTCATTAACGCAGGCATTACCATCGGAACTC
601 ------------+---------+---------+---------+---------+---------+ 660
    GAATTTGCACTCTTTGTCCTGCTTTCGACAAGTAATTGCGTCCGTAATGGTAGCCTTGAG
    L  K  R  E  K  Q  D  E  S  C  S  L  T  Q  A  L  P  S  E  L   -

AAGGTGAGCGCCGACAATGTCTCATTAACCGGTGCGGTAAGCCTCGCATCAATGCTGACG
661 ------------+---------+---------+---------+---------+---------+ 720
    TTCCACTCGCGGCTGTTACAGAGTAATTGGCCACGCCATTCGGAGCGTAGTTACGACTGC
    K  V  S  A  D  N  V  S  L  T  G  A  V  S  L  A  S  M  L  T   -

GAGATATTTCTCCTGCAACAAGCACAGGGAATGCCGGAGCCGGGGTGGGGAAGGATCACC
721 ------------+---------+---------+---------+---------+---------+ 780
    CTCTATAAAGAGGACGTTGTTCGTGTCCCTTACGGCCTCGGCCCCACCCCTTCCTAGTGG
    E  I  F  L  L  Q  Q  A  Q  G  M  P  E  P  G  W  G  R  I  T   -

GATTCACACCAGTGGAACACCTTGCTAAGTTTGCATAACGCGCAATTTTATTTGTTACAA
781 ------------+---------+---------+---------+---------+---------+ 840
    CTAAGTGTGGTCACCTTGTGGAACGATTCAAACGTATTGCGCGTTAAAATAAACAATGTT
    D  S  H  Q  W  N  T  L  L  S  L  H  N  A  Q  F  Y  L  L  Q   -
```

FIG. 1B

```
     CGCACGCCAGAGGTTGCCCGCAGCCGCGCCACCCCGTTATTAGATTTGATCAAGACAGCG
841  ------------+---------+---------+---------+---------+--------+ 900
     GCGTGCGGTCTCCAACGGGCGTCGGCGCGGTGGGGCAATAATCTAAACTAGTTCTGTCGC
      R  T  P  E  V  A  R  S  R  A  T  P  L  L  D  L  I  K  T  A   -

TTGACGCCCCATCCACCGCAAAAACAGGCGTATGGTGTGACATTACCCACTTCAGTGCTG
901  ------------+---------+---------+---------+---------+--------+ 960
     AACTGCGGGGTAGGTGGCGTTTTTGTCCGCATACCACACTGTAATGGGTGAAGTCACGAC
      L  T  P  H  P  P  Q  K  Q  A  Y  G  V  T  L  P  T  S  V  L   -

TTTATCGCCGGACACGATACTAATCTGGCAAATCTCGGCGGCGCACTGGAGCTCAACTGG
961  ------------+---------+---------+---------+---------+--------+ 1020
     AAATAGCGGCCTGTGCTATGATTAGACCGTTTAGAGCCGCCGCGTGACCTCGAGTTGACC
      F  I  A  G  H  D  T  N  L  A  N  L  G  G  A  L  E  L  N  W   -

ACGCTTCCCGGTCAGCCGGATAACACGCCGCCAGGTGGTGAACTGGTGTTTGAACGCTGG
1021 ------------+---------+---------+---------+---------+--------+ 1080
     TGCGAAGGGCCAGTCGGCCTATTGTGCGGCGGTCCACCACTTGACCACAAACTTGCGACC
      T  L  P  G  Q  P  D  N  T  P  P  G  G  E  L  V  F  E  R  W   -

CGTCGGCTAAGCGATAACAGCCAGTGGATTCAGGTTTCGCTGGTCTTCCAGACTTTACAG
1081 ------------+---------+---------+---------+---------+--------+ 1140
     GCAGCCGATTCGCTATTGTCGGTCACCTAAGTCCAAAGCGACCAGAAGGTCTGAAATGTC
      R  R  L  S  D  N  S  Q  W  I  Q  V  S  L  V  F  Q  T  L  Q   -

CAGATGCGTGATAAAACGCCGCTGTCATTAAATACGCCGCCCGGAGAGGTGAAACTGACC
1141 ------------+---------+---------+---------+---------+--------+ 1200
     GTCTACGCACTATTTTGCGGCGACAGTAATTTATGCGGCGGGCCTCTCCACTTTGACTGG
      Q  M  R  D  K  T  P  L  S  L  N  T  P  P  G  E  V  K  L  T   -

CTGGCAGGATGTGAAGAGCGAAATGCGCAGGGCATGTGTTCGTTGGCAGGTTTTACGCAA
1201 ------------+---------+---------+---------+---------+--------+ 1260
     GACCGTCCTACACTTCTCGCTTTACGCGTCCCGTACACAAGCAACCGTCCAAAATGCGTT
      L  A  G  C  E  E  R  N  A  Q  G  M  C  S  L  A  G  F  T  Q   -

ATCGTGAATGAAGCACGCATACCGGCGTGCAGTTTGTAA
1261 ------------+---------+--------- 1299         SEQ ID NO:1
     TAGCACTTACTTCGTGCGTATGGCCGCACGTCAAACATT
      I  V  N  E  A  R  I  P  A  C  S  L  *   -   SEQ ID NO:4
```

FIG. 2A

```
        CAATCCGAACCAGAGTTGAAGCTCGAATCCGTCGTGATCGTTTCCAGACACGGTGTTAGA
0001----+---------+---------+---------+---------+---------+---------+ 0060
        GTTAGGCTTGGTCTCAACTTCGAGCTTAGGCAGCACTAGCAAAGGTCTGTGCCACAATCT
         Q  S  E  P  E  L  K  L  E  S  V  V  I  V  S  R  H  G  V  R

GCCCCAACTAAAGCTACTCAATTGATGCAAGGTGTCACTCCTGACGCTTGGCCAACTTGG
0061----+---------+---------+---------+---------+---------+---------+ 0120
        CGGGGTTGATTTCGATGAGTTAACTACGTTCCACAGTGAGGACTGCGAACCGGTTGAACC
         A  P  T  K  A  T  Q  L  M  Q  G  V  T  P  D  A  W  P  T  W

CCAGTCAAATTGGGTTGGTTGACCCCAAGAGGTGGTGAATTGATTGCCTACTTGGGTCAC
0121----+---------+---------+---------+---------+---------+---------+ 0180
        GGTCAGTTTAACCCAACCAACTGGGGTTCTCCACCACTTAACTAACGGATGAACCCAGTG
         P  V  K  L  G  W  L  T  P  R  G  G  E  L  I  A  Y  L  G  H

TACCAAAGACAAAGATTGGTTGCTGACGGGTTGTTGGCCAAGAAGGGTTGTCCACAATCT
0181----+---------+---------+---------+---------+---------+---------+ 0240
        ATGGTTTCTGTTTCTAACCAACGACTGCCCAACAACCGGTTCTTCCCAACAGGTGTTAGA
         Y  Q  R  Q  R  L  V  A  D  G  L  L  A  K  K  G  C  P  Q  S

GGTCAAGTCGCTATTATTGCCGACGTTGACGAAAGAACCAGAAAGACCGGTGAAGCTTTC
0241----+---------+---------+---------+---------+---------+---------+ 0300
        CCAGTTCAGCGATAATAACGGCTGCAACTGCTTTCTTGGTCTTTCTGGCCACTTCGAAAG
         G  Q  V  A  I  I  A  D  V  D  E  R  T  R  K  T  G  E  A  F

GCCGCCGGTCTCGCCCCAGACTGTGCTATCACTGTCCACACCCAAGCGGACACTTCTTCC
0301----+---------+---------+---------+---------+---------+---------+ 0360
        CGGCGGCCAGAGCGGGGTCTGACACGATAGTGACAGGTGTGGGTTCGCCTGTGAAGAAGG
         A  A  G  L  A  P  D  C  A  I  T  V  H  T  Q  A  D  T  S  S

CCAGACCCATTGTTCAACCCATTGAAGACCGGTGTCTGTCAACTCGACAACTCTAACGTC
0361----+---------+---------+---------+---------+---------+---------+ 0420
        GGTCTGGGTAACAAGTTGGGTAACTTCTGGCCACAGACAGTTGAGCTGTTGAGATTGCAG
         P  D  P  L  F  N  P  L  K  T  G  V  C  Q  L  D  N  S  N  V

ACCGACGCCATTTTGTCCAGAGCCGGTGGTTCTATCGCTGGTTTCACCGGTCACAGACAA
0421----+---------+---------+---------+---------+---------+---------+ 0480
        TGGCTGCGGTAAAACAGGTCTCGGCCACCAAGATAGCGACCAAAGTGGCCAGTGTCTGTT
         T  D  A  I  L  S  R  A  G  G  S  I  A  G  F  T  G  H  R  Q

ACTGCTTTCAGAGAATTGGAGAGAGTCCTCAACTTCCCACAATCTAACCTCTGTTTGAAG
0481----+---------+---------+---------+---------+---------+---------+ 0540
        TGACGAAAGTCTCTTAACCTCTCTCAGGAGTTGAAGGGTGTTAGATTGGAGACAAACTTC
         T  A  F  R  E  L  E  R  V  L  N  F  P  Q  S  N  L  C  L  K

AGAGAGAAGCAAGACGAATCCTGTTCCTTGACCCAAGCCTTGCCATCTGAGTTGAAGGTC
0541----+---------+---------+---------+---------+---------+---------+ 0600
        TCTCTCTTCGTTCTGCTTAGGACAAGGAACTGGGTTCGGAACGGTAGACTCAACTTCCAG
         R  E  K  Q  D  E  S  C  S  L  T  Q  A  L  P  S  E  L  K  V

TCTGCTGACAACGTTTCTTTGACCGGTGCCGTCTCCTTGGCTTCCATGTTGACCGAGATC
0601----+---------+---------+---------+---------+---------+---------+ 0660
        AGACGACTGTTGCAAAGAAACTGGCCACGGCAGAGGAACCGAAGGTACAACTGGCTCTAG
         S  A  D  N  V  S  L  T  G  A  V  S  L  A  S  M  L  T  E  I

TTCCTCTTGCAACAAGCCCAAGGTATGCCAGAACCAGGTTGGGGTAGAATTACCGACTCC
0661----+---------+---------+---------+---------+---------+---------+ 0720
        AAGGAGAACGTTGTTCGGGTTCCATACGGTCTTGGTCCAACCCCATCTTAATGGCTGAGG
         F  L  L  Q  Q  A  Q  G  M  P  E  P  G  W  G  R  I  T  D  S

CACCAATGGAACACCTTGTTGTCCTTGCACAACGCTCAATTCTACTTGCTCCAAAGAACC
0721----+---------+---------+---------+---------+---------+---------+ 0780
        GTGGTTACCTTGTGGAACAACAGGAACGTGTTGCGAGTTAAGATGAACGAGGTTTCTTGG
         H  Q  W  N  T  L  L  S  L  H  N  A  Q  F  Y  L  L  Q  R  T

CCAGAGGTCGCTAGATCCAGAGCCACTCCACTCTTGGACCTCATTAAGACCGCCTTGACT
0781----+---------+---------+---------+---------+---------+---------+ 0840
        GGTCTCCAGCGATCTAGGTCTCGGTGAGGTGAGAACCTGGAGTAATTCTGGCGGAACTGA
         P  E  V  A  R  S  R  A  T  P  L  L  D  L  I  K  T  A  L  T
```

FIG. 2B

```
          CCACACCCACCACAAAAGCAAGCTTACGGTGTTACCTTGCCAACCTCCGTCTTGTTCATT
0841------+---------+---------+---------+---------+---------+ 0900
          GGTGTGGGTGGTGTTTTCGTTCGAATGCCACAATGGAACGGTTGGAGGCAGAACAAGTAA
          P  H  P  P  Q  K  Q  A  Y  G  V  T  L  P  T  S  V  L  F  I

GCCGGTCATGACACCAACTTGGCTAACTTGGGTGGTGCCCTCGAACTCAACTGGACTTTG
0901------+---------+---------+---------+---------+---------+ 0960
          CGGCCAGTACTGTGGTTGAACCGATTGAACCCACCACGGGAGCTTGAGTTGACCTGAAAC
          A  G  H  D  T  N  L  A  N  L  G  G  A  L  E  L  N  W  T  L

CCAGGTCAACCAGACAACACCCCACCAGGTGGTGAATTGGTTTTCGAAAGATGGAGAAGA
0961------+---------+---------+---------+---------+---------+ 1020
          GGTCCAGTTGGTCTGTTGTGGGGTGGTCCACCACTTAACCAAAAGCTTTCTACCTCTTCT
          P  G  Q  P  D  N  T  P  P  G  G  E  L  V  F  E  R  W  R  R

CTCTCCGACAACTCTCAATGGATTCAAGTCTCTTTGGTCTTCCAAACCTTGCAACAAATG
1021------+---------+---------+---------+---------+---------+ 1080
          GAGAGGCTGTTGAGAGTTACCTAAGTTCAGAGAAACCAGAAGGTTTGGAACGTTGTTTAC
          L  S  D  N  S  Q  W  I  Q  V  S  L  V  F  Q  T  L  Q  Q  M

AGAGACAAGACTCCACTCTCCTTGAACACCCCACCAGGTGAGGTCAAGTTGACCCTCGCT
1081------+---------+---------+---------+---------+---------+ 1140
          TCTCTGTTCTGAGGTGAGAGGAACTTGTGGGGTGGTCCACTCCAGTTCAACTGGGAGCGA
          R  D  K  T  P  L  S  L  N  T  P  P  G  E  V  K  L  T  L  A

GGTTGTGAAGAAAGAAACGCCCAAGGTATGTGTTCTTTGGCCGGTTTCACTCAAATCGTT
1141------+---------+---------+---------+---------+---------+ 1200
          CCAACACTTCTTTCTTTGCGGGTTCCATACACAAGAAACCGGCCAAAGTGAGTTTAGCAA
          G  C  E  E  R  N  A  Q  G  M  C  S  L  A  G  F  T  Q  I  V

AACGAAGCTAGAATCCCAGCCTGTTCTTTGTAA
1201------+---------+---------+---    SEQ ID NO:2
          TTGCTTCGATCTTAGGGTCGGACAAGAAACATT
          N  E  A  R  I  P  A  C  S  L  *   SEQ ID NO:3
```

FIG. 3

OLIGO ID NO.1:
 5'-CTGCAGGGAGANARYTTNARYTCNGGYTCNSWYTGCAT-3'

OLIGO ID NO.2:
 5'-NARNSWRCANGCNGGDATTAATCTAGA-3'

OLIGO ID NO.3:
 5'-AATCGCCTATCTCGGACATTAC-3'

OLIGO ID NO.4:
 5'-TGCCTTAAACGTGAGAAACAG-3'

OLIGO ID NO.5:
 5'-CCTGGGTATGTACGGTTATTG-3'

OLIGO ID NO.6:
 5'-GGGTAATGTCACACCATACGC-3'

OLIGO ID NO.7:
 5'-CCATGGCAATCCGAACCAGAGTTGA-3'

OLIGO ID NO.8:
 5'-TACGTATTACAAAGAACAGGCTGGGATTCTAGCT-3'

OLIGO ID NO.9:
 5'-GGGAATTCCAATCCGAACCAGAGTTGAAG-3'

OLIGO ID NO.10:
 5'-GCGGCCGCTTACAAAGAACAGGCTG-3'

OLIGO ID NO.11:
 5'-GCTGCAGCAATCCGAACCAGAGTTGA-3'

OLIGO ID NO.12:
 5'-GCGGCCGCTTACAAAGAACAGGCTG-3'

OLIGO ID NO.13:
 5'-GGAGATCTCAATCCGAACCAGAGTTGAAGCT-3'

OLIGO ID NO.14:
 5'-GCGGCCGCTTACAAAGAACAGGCTG-3'

Note: K: G or T/U;  S: C or G;  W: A or T;  Y: C or T/U;  M: A or C;  N: A,C,G or T/U;  R: A or G

FIG. 4

```
                   Signal peptides
K12 app A     1  MKAILIPFLS LLIPLTPQSA FAQSEPELKL ESVVIVSRHG VRAPTKATQL MQDVTPDAWP
W-Phytase     1  MKAILIPFLS LLIPLTPQSA FAQSEPELKL ESVVIVSRHG VRAPTKATQL MQGVTPDAWP
Lei appA2     1  MKAILIPFLS LLIPLTPQSA FAQSEPELKL ESVVIVSRHG VRAPTKATQL MQDVTPDAWP K12 app A    61  TWPVKLGWLT PRGGELIAYL GHYQRQRLVA DGLLAKKGCP QSGQVAIIAD VDERTRKTGE
W-Phytase    61  TWPVKLGWLT PRGGELIAYL GHYQRQRLVA DGLLAKKGCP QSGQVAIIAD VDERTRKTGE
Lei appA2    61  TWPVKLGWLT PRGGELIAYL GHYQRQRLVA DGLLAKKGCP QPGQVAIIAD VDERTRKTGE K12 app A   121  AFAAGLAPDC AITVHTQADT SSPDPLFNPL KTGVCQLDNA NVTDAILSRA GGSIADFTGH
W-Phytase   121  AFAAGLAPDC AITVHTQADT SSPDPLFNPL KTGVCQLDNS NVTDAILSRA GGSIAGFTGH
Lei appA2   121  AFAAGLAPDC AITVHTQADT SSPDPLFNPL KTGVCQLDVA NVTDAILSRA GGSIADFTGH K12 app A   181  RQTAFRELER VLNFPQSNLC LKREKQDESC SLTQALPSEL KVSADNVSLT GAVSLASMLT
W-Phytase   181  RQTAFRELER VLNFPQSNLC LKREKQDESC SLTQALPSEL KVSADNVSLT GAVSLASMLT
Lei appA2   181  RQTAFRELER VLNFSQLNLC LNREKQDESC SLTQALPSEL KVSADNVSLT GAVSLASMLT K12 app A   241  KIFLLQQAQG MPEPGWGRIT DSHQWNTLLS LHNAQFYLLQ RTPEVARSRA TPLLDLIKTA
W-Phytase   241  EIFLLQQAQG MPEPGWGRIT DSHQWNTLLS LHNAQFYLLQ RTPEVARSRA TPLLDLIKTA
Lei appA2   241  EIFLLQQAQG MPEPGWGRIT DSHQWNTLLS LHNAQFYLLQ RTPEVARSRA TPLLDLIMAA K12 app A   301  LTPHPPQKQA YGVTLPTSVL FIAGHDTNLA NLGGALELNW TLPGQPDNTP PGGELVFERW
W-Phytase   301  LTPHPPQKQA YGVTLPTSVL FIAGHDTNLA NLGGALELNW TLPGQPDNTP PGGELVFERW
Lei appA2   301  LTPHPPQKQA YGVTLPTSVL FIAGHDTNLA NLGGALELNW TLPGQPDNTP PGGELVFERW K12 app A   361  RRLSDNSQWI QVSLVFQTLQ QMRDKTPLSL NTPPGEVKLT LAGCEERNAQ GMCSLAGFTQ
W-Phytase   361  RRLSDNSQWI QVSLVFQTLQ QMRDKTPLSL NTPPGEVKLT LAGCEERNAQ GMCSLAGFTQ
Lei appA2   361  RRLSDNSQWI QVSLVFQTLQ QMRDKTPLSL NTPPGEVKLT LAGCEERNAQ GMCSLAGFTQ K12 app A   421  IVNEARIPAC SL    E.Coli K12 appA Phytase gene(M58708)     (SEQ ID NO:5)
W-Phytase   421  IVNEARIPAC SL    E.coli Non-K12 W Strain Phytase Gene   (SEQ ID NO:4)
Lei appA2   421  IVNEARIPAC SL    Pig Colon E.coli Phytase Gene (Patent No.6511699)(SEQ ID NO:6)
```

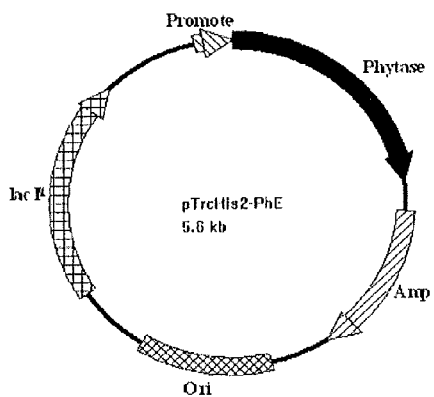
FIG. 5
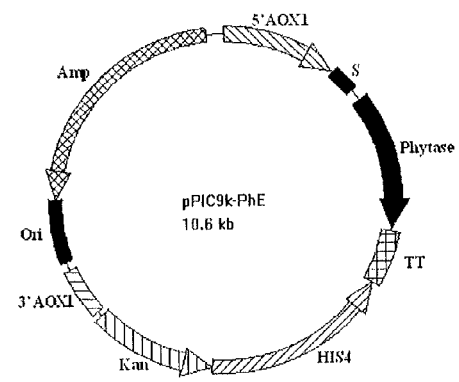
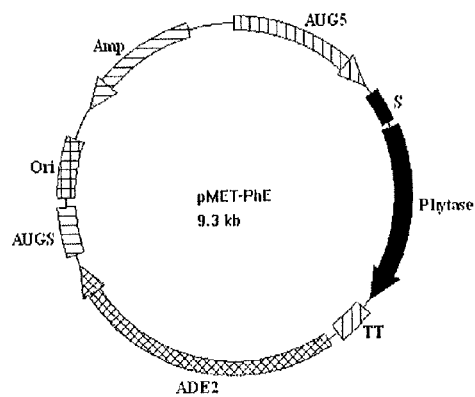
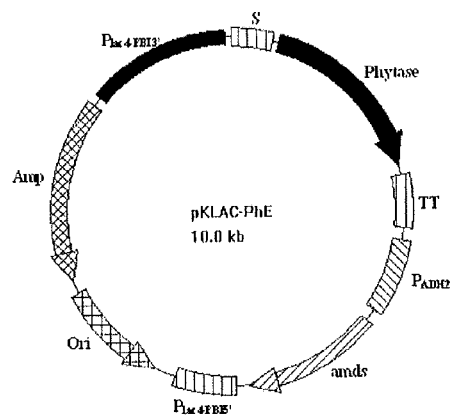

Mark: molecular mark
1: Supernate at 28 hr
2: Supernate at 42 hr
3: Supernate at 50 hr
4: Supernate at 69 hr
5: Supernate at 89 hr Mark: molecular mark, 1: expressed phytase;

THERMOTOLERANT NON-K12 *ESCHERICHIA COLI* PHYTASE AND ITS PRODUCTION

TECHNICAL FIELD

The present invention relates to the fields of molecular biology, biochemistry, fermentation and post-process of phytase. More specifically, the present invention relates to cloning and expression of a novel Non-K12 *Escherichia coli* gene coding for thermotolerant phytate hydratase enzyme, phytase.

BACKGROUND OF THE INVENTION

Phytases (myo-inositol hexakisphosphate phosphohydrolase: EC 3.1.3.8) are enzymes that hydrolyze phytate (myo-inositol hexakisphosphate) to myo-inositol and inorganic phosphate. The enzymes are known to be valuable feed additives. At the close of the twentieth century, annual sales of phytase as an animal feed additive were estimated to exceed $150 million and were growing.

Poultry and pig diets are currently based primarily on cereals, legumes, and oilseed products. About two-thirds of phosphorus (P) present in these feedstuffs occurs as phytates, the salts of phytic acid. Phytate phosphorus in plants is a mixed calcium-magnesium-potassium salt of phytic acid that is present as chelate and its solubility is very low. Phosphorus in this form is poorly digestible for monogastric animals such as human, swine, and poultry.

For the utilization of phytate phosphorus and minerals and trace elements bound in phytic acid complexes, hydrolysis of the ester-type bonded phosphate groups of phytic acid by phytase is necessary. Phytases belong to a special group of phosphatases which are capable of hydrolyzing phytate to a series of lower phosphate esters of myo-inositol and phosphate. Two types of phytases are known: 3-phytase and 6-phytase, indicating the initial attack of the susceptible phosphate ester bond. Although monogastric animals lack sufficient phytase to effectively utilize phytate phosphorous, many fungi, bacteria and yeasts produce phytase that can be used to supplement animal rations.

The beneficial effects of supplementary phytases on phosphorus digestibility and animal performance have been well documented (Mroz et al., 1994; Kornegay et al., 1996; Rao et al., 1999; Ravindran et al., 1999). The efficacy of enzyme preparation depends not only on the type, inclusion rate and level of activity present, but also on the ability of the enzyme to maintain its activity in the different conditions encountered through the gastrointestinal tract and the conditions used for the pre-treatment of a food or feed formulation.

Although numerous phytases are available for use as a supplement, many of the enzymes have certain disadvantages. For example, many of the currently used phytases lose activity during feed pelleting processes due to heat treatment. Additionally, many of the currently used phytases are not adequate in instability for proteases in animal digestion systems such as pepsins and chymotrypsins.

There is a need for a phytase with improve properties for use in animal feed and food processing.

SUMMARY OF THE INVENTION

Accordingly, in one aspect, the present invention provides an isolated nucleic acid molecule comprising a nucleotide sequence selected from the group consisting of:

a) a nucleotide sequence encoding a polypeptide comprising the amino acid as set forth in SEQ ID NO: 3;
b) a nucleotide sequence hybridizing to a) under a stringent hybridization condition, wherein said nucleotide sequence encoding a polypeptide having the activity of a Non-K12 *Escherichia coli* phytase; or
c) a nucleotide sequence complementary to either of a) and b).

In one embodiment of the invention, the isolated nucleic acid molecule comprises a nucleotide sequence selected from the group consisting of:

a) a nucleotide sequence consisting of nucleotides 67-1296 as set forth in SEQ ID NO: 1;
b) a nucleotide sequence consisting of nucleotides 1-1230 as set forth in SEQ ID NO: 2;
c) a nucleotide sequence as set forth in SEQ ID NO: 1;
d) a nucleotide sequence hybridizing to any of a) to c) under a stringent condition, and encoding a polypeptide having the activity of a Non-K12 *Escherichia coli* phytase; or
e) a nucleotide sequence complementary to any of a) to d)

In another aspect, the present invention provides a vector, comprising the isolated nucleic acid molecule of the invention, preferably, said vector is an expression vector. For example, said vector may be selected from the group consisting of pTrcHis2-PhE, pPIC9K-PhE, pMET-PhE and pKLAC-PhE.

In a further aspect, the present invention provides an isolated cell comprising an isolated nucleic acid molecule according to the invention, preferably, said isolated nucleic acid molecule is comprised in an expression vector. Preferably, said cell is a yeast cell. For example, said cell may be selected from the group consisting of *Escherichia coli*, *Pichia pastoris*, *Pichia methanolica* and *Kluyeromyces lactis*. More specifically, the cell can be derived from a strain selected from the group consisting of *E. coli* MG1655, *P. pastoris* GS115, *P. methanolica* PMAD16 and *Kluyeromyces lactis* GG799. In one embodiment of the invention, the cell is a strain selected from the group consisting of *E. coli* MG1655 transformed with pTrcHis2-PhE, *P. pastoris* SMD1168 transformed by pPIC9K-PhE, *P. methanolica* PMD16 transformed by pMET-PhE and *Kluyeromyces lactis* GG799 transformed by pKLAC-PhE.

In a further aspect, the present invention provides a polypeptide comprising an amino acid sequence selected from the group consisting of:

a) an amino acid sequence as set forth in SEQ ID NO: 3; or
b) an amino acid sequence having an identity of at least 99% to SEQ ID NO: 3; wherein said polypeptide has the activity of Non-K12 *Escherichia coli* phytase.

In a further aspect, the present invention provides a process for production of a Non-K12 *Escherichia coil* phytase by fermentation, comprising a step of cultivating a cell comprising the isolated nucleic acid molecule of the invention under a condition effective for expression to obtain a polypeptide having the activity of Non-K12 *Escherichia coli* phytase. Preferably, said cell is a strain selected from the group consisting of *E. coli* MG1655 transformed with pTrcHis2-PhE, *P. pastoris* SMD1168 transformed by pPIC9K-PhE, *P. methanolica* PMD16 transformed by pMET-PhE and *Kluyeromyces lactis* GG799 transformed by pKLAC-PhE.

BRIEF DESCRIPTION OF THE DRAWINGS

FIGS. 1A and 1B show a nucleic acid sequence (SEQ ID NO: 1) encoding the non-K12 *Escherichia coli* phytase isolated from the strain *Escherichia coli* ATCC 9637 and the amino acid sequence of the encoded protein (SEQ ID NO: 4)

in an embodiment of the invention. The signal peptide is underlined. The nucleic acid sequence encoding the mature protein is from nucleotide 67 to nucleotide 1296. The stop codon TAA is denoted by "*".

FIGS. 2A and 2B show a nucleic acid sequence (SEQ ID NO: 2) encoding the non-K12 phytase and the amino acid sequence of the encoded protein (SEQ ID NO: 3) in another embodiment of the invention, wherein the codons are optimized for gene expression in yeast systems. The nucleic acid sequence encoding the mature protein is from nucleotide 1 to nucleotide 1230. The stop codon TAA is denoted by "*".

FIG. 3 shows the sequences of the primers used for cloning the nucleic acid molecules of the invention in the exemplified embodiments of the invention.

FIG. 4 shows the comparison of amino acid sequence between the Non-K12 phytase of the invention (SEQ ID NO: 4) and two known phytases (SEQ ID NOS: 5 and 6).

FIG. 5 shows the construction maps of the recombinant expression plasmids constructed in several embodiments of the present invention. In the plasmid pTrcHis2-PhE, the insert "Phytase" has the sequence of SEQ ID NO: 1, while the insert "Phytase" in pPIC9k-PhE, pMET-PhE and pKLAC-PhE has the sequence of SEQ ID NO: 2.

Figure 6:
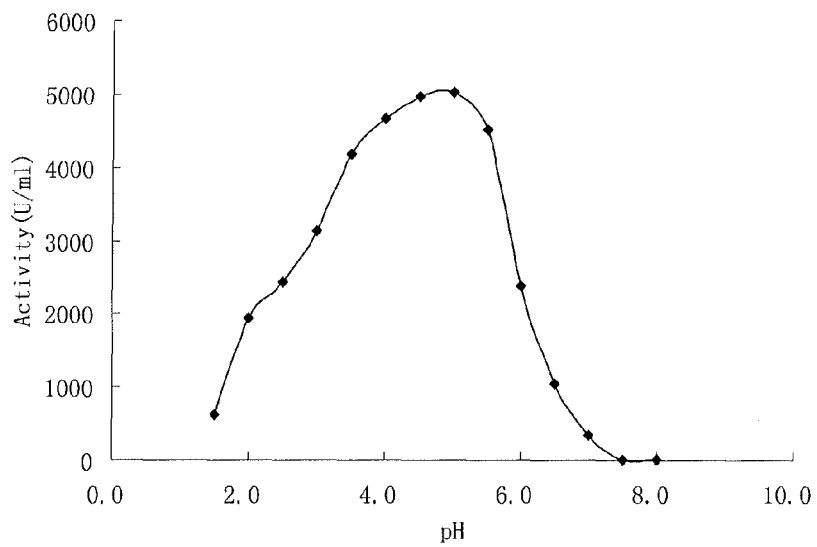

FIG. 6 shows the Non-K12 phytase activities at different pH.

Figure 7:
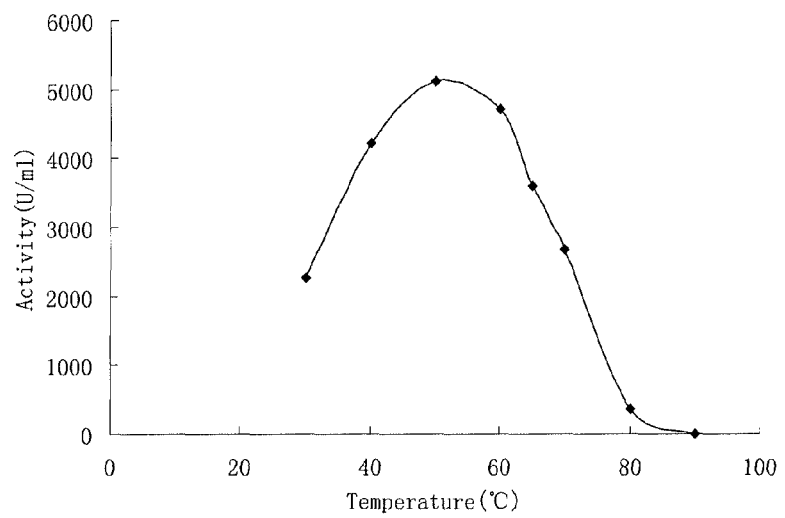

FIG. 7 shows the Non-K12 phytase activity at different temperatures.

Figure 8:
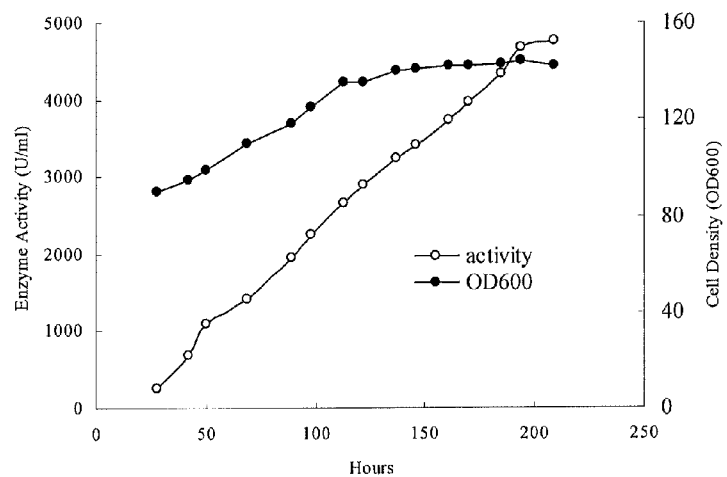

FIG. 8 shows the Non-K12 phytase activities at different fermentation times.

Figure 9:
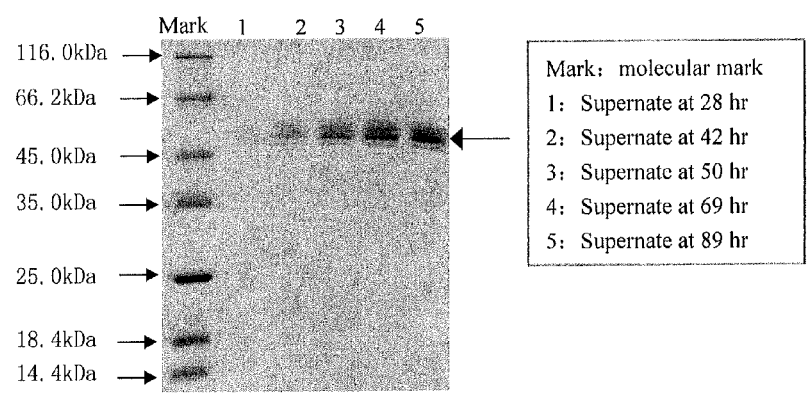

FIG. 9 shows the Non-K12 phytase product on SDS-PAGE of samples at different time points of a fermentation according to the present invention.

Figure 10:
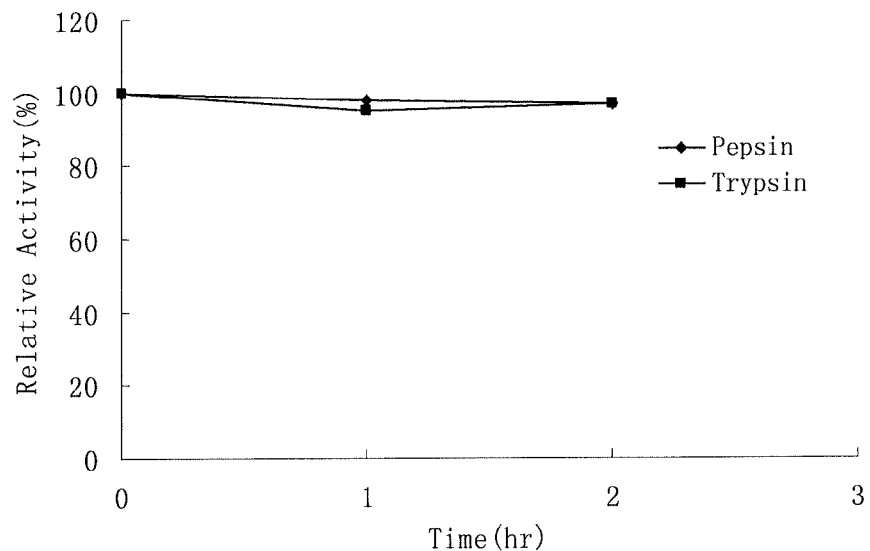

FIG. 10 shows the Non-K12 phytase activity after treatment with the indicated proteases.

Figure 11:
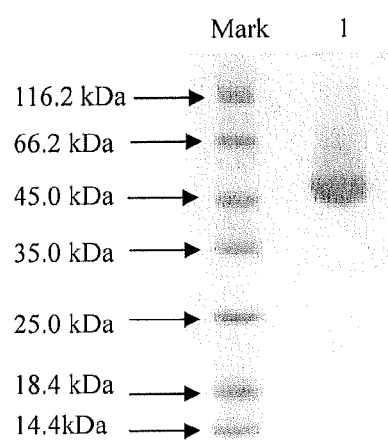

FIG. 11 shows the Molecular weight of the phytase secreted by *Pichia pastoris* in an embodiment of the invention.

Figure 12:
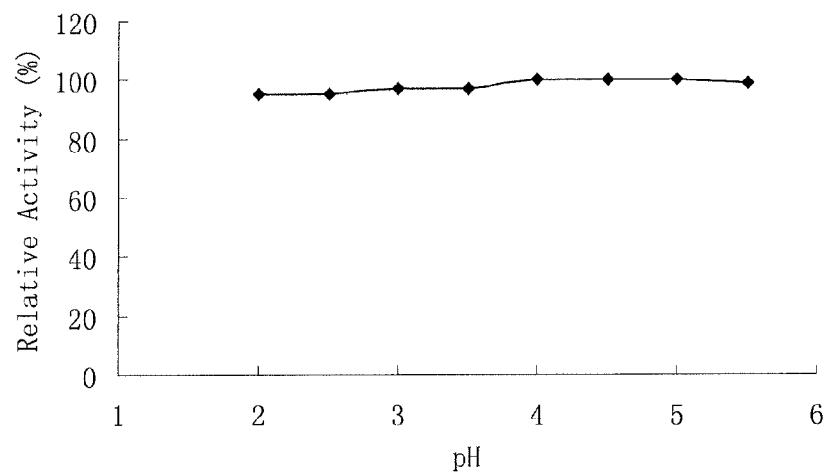

FIG. 12 shows the pH-tolerance of the expressed phytase in an embodiment of the invention.

Figure 13:
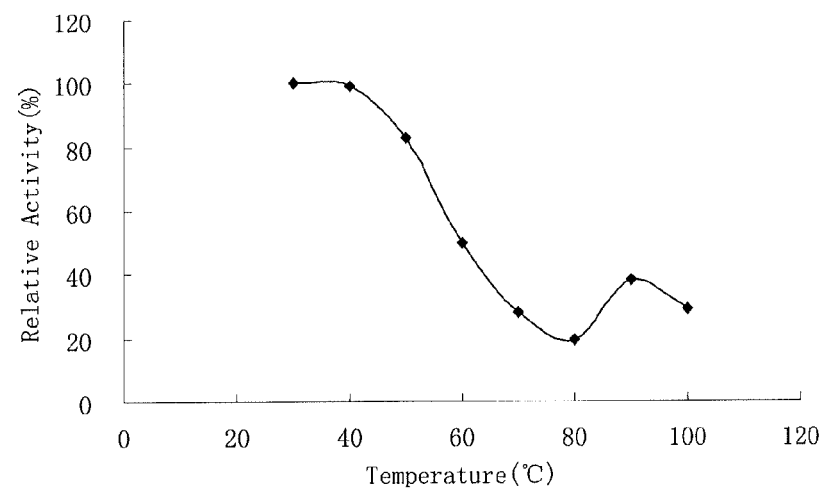

FIG. 13 shows the thermotolerance of the expressed phytase in an embodiment of the invention.

Figure 14:
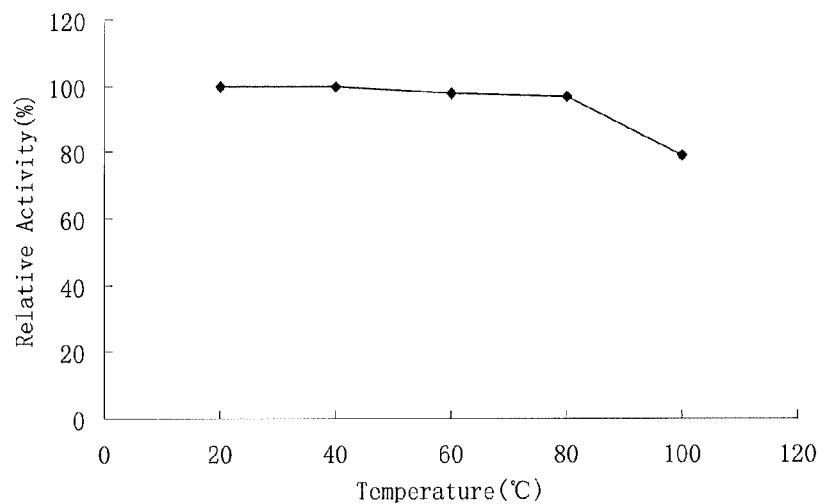

FIG. 14 shows the thermotolerance of a dried formulated phytase of the invention.

Figure 15:
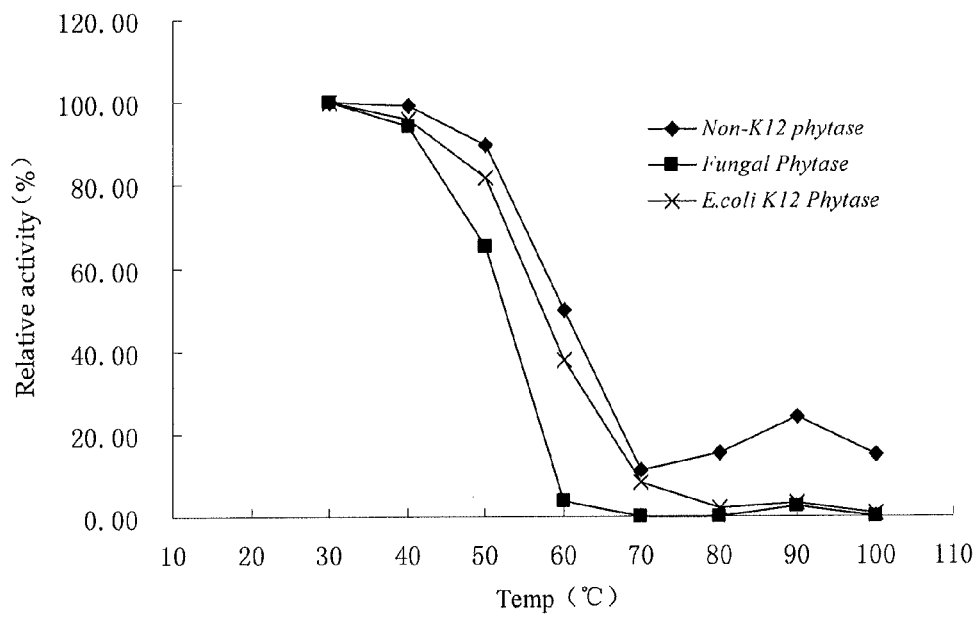

FIG. 15: comparison of the thermotolerance between the Non-K12 phytase of the invention and the *E. coli* K12 phytase and the fungal phytase from *Aspergillus niger*.

Figure 16:
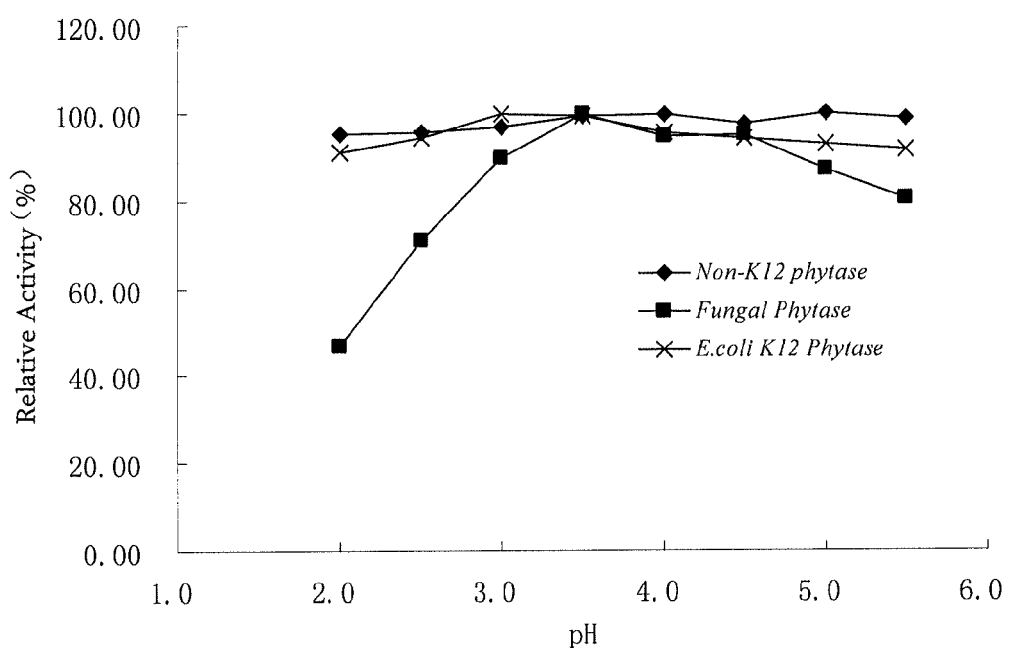

FIG. 16: comparison of the pH-tolerance between the Non-K12 phytase of the invention and the *E. coli* K12 phytase and the fungal phytase from *Aspergillus niger*.

DETAILED DESCRIPTION OF THE INVENTION

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

The term "thermotolerant" characterizes an enzyme that retains activity despite exposure to a given temperature.

As used herein, the term "pTrcHis2-PhE" refers to the plasmid pTrcHis2 (Invitrogen Biotechnology Co., Ltd) containing a nucleotide sequence as set forth in SEQ ID NO: 1 under the control of LacO promoter and a pBR322 origin, and bla(Apm) gene for DNA replication and transformation selection as shown in FIG. 5.

As used herein, the term "pPIC9K-PhE" refers to the plasmid pPIC9K (Invitrogen Biotechnology Co., Ltd) containing the nucleotide sequence as set forth in SEQ ID NO: 2 in the orientation as shown in FIG. 5.

As used herein, the term "pMET-PhE" refers to the plasmid pMETalphaA (Novagen, Inc.) containing the nucleotide sequence as set forth in SEQ ID NO: 2 in the orientation as shown in FIG. 5.

As used herein, the term "pKLAC-PhE" refers to the plasmid pKLAC(New England Biolabs, Inc.) containing the nucleotide sequence as set forth in SEQ ID NO: 2 in the orientation as shown in FIG. 5.

As used herein, an "isolated nucleic acid fragment" or "isolated polynucleotide" is a polymer of RNA or DNA that is single- or double-stranded, optionally containing synthetic, non-natural, or altered nucleotide bases. An isolated nucleic acid fragment in the form of a polymer of DNA may be comprised of one or more segments of cDNA, genomic DNA, or synthetic DNA.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in FIGS. 1 and 2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403 410 (1990), and DNAS-TAR (DNASTAR, Inc. 1228 S. Park St. Madison, Wis. 53715 USA), and the FASTA program incorporating the Smith-Waterman algorithm (W. R. Pearson, Comput. Methods Genome Res., [Proc. Int. Symp.] (1994), Meeting Date 1992, 111 20. Editor(s): Suhai, Sandor. Publisher: Plenum, New York, N.Y.). The term "MEME" refers to a software program used to identify conserved diagnostic motifs based on a hidden Markov model (Timothy L. Bailey and Charles Elkan, Fitting a mixture model by expectation maximization to discover motifs in biopolymers, Proceedings of the Second International Conference on Intelligent Systems for Molecular Biology, pp. 28 36, AAAI Press, Menlo Park, Calif. (1994)). "MAST" (Timothy L. Bailey and Michael Gribskov, "Combining evidence using p-values: application to sequence homology searches" Bioinformatics, Vol. 14, pp. 48 54 (1998)) is a program that takes the output from the MEME program and searches the identified motifs against the protein databases such as EMBL and SwissProt. Within the context of this application it will be understood that where sequence analysis software is used for analysis, the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described, for example, by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984) (hereinafter "Silhavy"); and by Ausubel, F. M. et al., Current Protocols in Molecular Biology, published by Greene Publishing Assoc. and Wiley-Interscience (1987) (hereinafter "Ausubel").

The present invention provides a polynucleotide isolated from *Escherichia coli* ATCC 9637 (American Type Culture Collection (ATCC), P.O. Box 1549, Manassas, Va. 20108, USA) and a synthetic nucleic acid sequence that encode the said polypeptide. The isolated polypeptide is a Non-K12 *Escherichia coli* phytase. When expressed, the phytase hydrates phytates into the corresponding myo-inositol and inorganic phosphate. The invention also provides transformed microbial host cells expressing the polypeptides. The invention further provides a method for producing the polypeptide catalysts using the transformed microbes and a method for using the catalysts for converting phytates to the myo-inositol and inorganic phosphate In the context of the present invention, the terms "a Non-K12 *Escherichia coli* phytase", "a Non-K12 *E. coli* phytase", "a Non-K12 phytase" and "a thermotolerant phytase" are used interchangeably as referring to a thermotolerant phytase which retains at least 17% activity as a phytase at a temperature up to 80 for 1 hr, more preferably at least 33% activity at a temperature up to 90 for 1 hr, even more preferably at least 26% activity at a temperature up to 100 for 1 hr, which has gastric stability against acid environment and proteases in animal digestion system.

In one embodiment, the invention provides a method to prepare a thermotolerant phytase. The method comprises expressing in a microbial host cell an expression cassette comprising a promoter linked to a nucleic acid molecule encoding a thermotolerant phytase. The microbial host cell may be a prokaryotic cell, such as a bacterial cell (e.g., *Escherichia* or *Bacillus*), yeast (e.g., *Saccharomyces, Schizosaccharomyces, Pichia* or *Kluyeromyces lactis*) cell. In one preferred embodiment, the microbial cell which is employed to prepare the recombinant thermotolerant phytase yields a glycosylated form of the recombinant thermotolerant phytase.

The invention provides methods of cloning and sequencing a nucleic acid molecule encoding a thermotolerant phytase which has 1296 nucleic acids coding for 432 amino acids including a signal peptide of 22 amino acids. Sequence comparison (FIG. 4, wherein "W-Phytase" refers to the Non-K12 phytase of the present invention) shows that the present invention provided a novel phytase polypeptide.

It is preferred that the polynucleotide that encodes the thermotolerant phytase (the first polynucleotide) is operably linked to at least one regulatory sequence, such as a promoter, an enhancer, a termination sequence, or any combination thereof, and, optionally, to a second polynucleotide encoding a signal sequence, which directs the phytase encoded by the first polynucleotide to a particular cellular location e.g., an extracellular location. Promoters can be constitutive promoters or inducible (conditional) promoters.

A parent polynucleotide may be obtained from any source including bacterial or fungal nucleic acid, and any method may be employed to prepare a synthetic polynucleotide of the invention from a selected parent polynucleotide, e.g., combinatorial mutagenesis, recursive mutagenesis and/or DNA shuffling.

In one embodiment, the present invention provides a nucleotide sequence hybridizing to the indicated sequences, such as SEQ ID NO: 1 or SEQ ID NO: 2, under a stringent hybridization condition. The "stringent hybridization condition" can be a conventional one as previously described in the relevant articles, e.g., Molecular Cloning, A Laboratory Manual, 2nd Edition (1989), Sambrook et al, Cold Spring Harbor Laboratory Press, Cold Spring Harbor, N.Y.). For example, a stringent hybridization condition may be 0.1.times.SSC, 0.1% SDS, 65. And, other exemplary conditions for hybridization include (1) high stringency: 0.1.times.SSPE, 0.1% SDS, 65; (2) medium stringency: 0.2.times.SSPE, 0.1% SDS, 50; and (3) low stringency: 1.0.times. SSPE, 0.1% SDS, 50. Obviously, equivalent stringencies may be achieved using alternative buffers, salts and temperatures.

Thus, in one embodiment of the invention, the thermotolerant phytase has one or more amino acid substitutions relative to a corresponding (reference) phytase, which substitutions are associated with the retention of activity at temperatures equal to or greater than 60. Preferably, the thermotolerant phytase has at least 17% activity remained under 80 for 1 hr, more preferably at least 33% activity at 90 for 1 hr, even more preferably at least 26% activity at 100 for 1 hr. An exemplary thermotolerant phytase of the invention is the Non-K12 *Escherichia coli* phytase having the amino acid sequence of SEQ ID NO: 3 (also see FIG. 1).

In one embodiment, the present invention also provides a polypeptide comprising an amino acid sequence having a certain identity to SEQ ID NO: 3; wherein said polypeptide has the activity of Non-K12 *Escherichia coli* phytase. The term "identity" when used in connection with the polypeptide of the present invention, is defined as the percentage of amino acid residues in a candidate sequence that are identical with a subject sequence (such as SEQ ID NO: 3), after aligning the candidate and subject sequences to achieve the maximum percent identity. Amino acid sequence identity can be determined by many known methods, such as the alignment method of Needleman and Wunsch (J. Mol. Biol. 48:443-453 (1970)), or using commercially available programs. It is well understood that many levels of sequence identity are useful in identifying related polypeptide sequences. As contemplated by the present invention, the useful identities include but are not limited to 50%, 55%, 60%, 65%, 70%, 75%, 80%, 85%, 86%, 90%, 95%, 99% or 100, and also the values between them.

Vectors, which comprise the expression cassette or polynucleotide of the invention and transformed microbial cells comprising the polynucleotide, expression cassette or vector of the invention, are also provided by this invention. A vector of the invention can encode more than one polypeptide including more than one thermotolerant phytase or may encode a fusion polypeptide comprising the thermotolerant phytase of the invention, and a transformed microbial cell may comprise one or more vectors of the invention. The transformed cells of the invention are useful for preparing the recombinant thermotolerant phytase of the invention. Accordingly, the invention provides thermotolerant phytase isolated from the transformed microbial cells of the invention, as well as synthetically prepared phytase(s).

Further, the invention provides the preparation of thermotolerant phytase via fermentation of a yeast strain comprising the Non-K12 *Escherichia coli* phytase gene. By the provided process of fermentation for production of phytase, the yield of the protein reaches 2.7 g/L. The phytase, which is estimated to be partially glycosylated, showed a molecular weight of 52 kD on SDS-PAGE (example 7). The optimal pH range for the phytase of the invention is pH2-7.5, preferably pH 3-6.

Further, as a phytase of the invention is capable of surviving the heat conditioning step encountered in a commercial pellet mill during feed formulation, the invention provides a method on making animal feed, e.g., hard granular feed pellets comprising the thermotolerant phytase. To make feed, the formulated phytase may be mixed with feed components, the mixture steam conditioned in a pellet mill such that at least 60% of the pre-heat treated enzymatic activity is retained, and the feed extruded through a pellet dye. The phytase may thus be used as a supplement in animal feed by itself, in addition with vitamins, minerals, other feed enzymes, agricultural co-products (e.g., wheat middling or corn gluten meal), or in a combination therewith. The phytase of the invention may also be added to mash diets, i.e., diets that have not been through a pelletizer.

Because the currently available commercial phytase enzymes are not thermotolerant, they are often applied after pelleting, generally via spraying an solution of the phytase onto the surface of pelleted feed. Problems found with spraying methods are that only a low percentage of the pellets are contacted with the enzyme, the enzyme is only present on the surface of the coated pellets, and feed mills need to invest in and operate complex spraying machinery. In contrast, the thermotolerant phytase of the invention, which has high specific activity of 3146 U/mg, may be added prior to pelleting, thereby facilitating production of a feed with an improved distribution of the enzyme.

Microbial Recombinant Expression

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources.

Examples of host strains include but are not limited to bacterial, fungal or yeast species such as *Aspergillus, Trichoderma, Saccharomyces, Pichia, Candida, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus*, and *Staphylococcus*. In another embodiment, suitable host strains are selected from the group consisting of *Aspergillus, Saccharomyces, Pichia, Candida, Hansuela, Bacillus, Rhodococcus, Streptomyces, Brevibacterium, Corynebacteria, Escherichia, Pseudomonas, Methylomonas, Synechocystis*, and *Klebsiella*. In a further embodiment, suitable host strains are selected from the group consisting of *Bacillus, Rhodococcus, Escherichia, Pseudomonas, Klebsiella*, and *Methylomonas*.

Microbial expression systems and expression vectors containing regulatory sequences that direct high level expression of foreign proteins are well known to those skilled in the art. Any of these could be used to construct chimeric genes for expression of the phytases of the present invention. These chimeric genes could then be introduced into appropriate a host via transformation to provide high-level expression of the enzyme Accordingly it is expected, for example, that introduction of chimeric genes encoding the instant bacterial phytase under the control of an appropriate promoter, will demonstrate increased phytate to phosphate and myo-inositol conversion. It is contemplated that it will be useful to express the instant genes both in natural host cells as well as in a heterologous host. Introduction of the present genes into native hosts will result in altered levels of existing phytase activity.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, IP.sub.L, IP.sub.R, T7, tac, and trc (useful for expression in *Escherichia coli*) as well as the amy, apr, npr promoters and various phage promoters useful for expression in *Bacillus*. Additionally, the deoxy-xylulose phosphate synthase or methanol dehydrogenase operon promoter (Springer et al., FEMS Microbiol Lett 160:119 124 (1998)), the promoter for polyhydroxyalkanoic acid synthesis (Foellner et al., Appl. Microbiol. Biotechnol. 40:284 291 (1993)), promoters identified from native plasmids in methylotrophs (EP 296484), promoters identified from methanotrophs (PCT/US03/33698), and promoters associated with antibiotic resistance [e.g., kanamycin (Springer et al., supra; Ueda et al., Appl. Environ. Microbiol. 57:924 926 (1991)) or tetracycline (U.S. Pat. No. 4,824,786)] are suitable for expression of the present coding sequences, especially in C1 metabolizers.

Termination control regions may also be derived from various genes native to the preferred hosts. Optionally, a termination site may be unnecessary; however, it is most preferred if included.

Methods of manipulating genetic pathways are common and well known in the art. Selected genes in a particularly pathway may be up-regulated or down-regulated by variety of methods. Additionally, competing pathways may be eliminated or sublimated by gene disruption and similar techniques.

Once a key genetic pathway has been identified and sequenced, specific genes may be up-regulated to increase the output of the pathway. For example, additional copies of the targeted genes may be introduced into the host cell on multi-copy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively, it may be necessary to reduce or eliminate the expression of certain genes in a pathway or in competing pathways that may serve as competing sinks for energy or carbon. Methods of down-regulating genes for this purpose have been explored. Where sequence of the gene to be disrupted is known, one of the most effective methods of gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell (Hamilton et al., J. Bacteriol. 171: 4617 4622 (1989); Balbas et al., Gene 136:211 213 (1993); Gueldener et al., Nucleic Acids Res. 24:2519 2524 (1996); and Smith et al., Methods Mol. Cell. Biol. 5:270 277(1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of anti-sense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as HNO.sub.2 and NH.sub.2OH, as well as agents that affect replicating DNA such as acridine dyes, notable for causing frameshift mutations. Specific methods for creating mutants using radiation or chemical agents are well documented in the art. (See for example, Thomas D. Brock in Biotechnology: A Textbook of Industrial Microbiology, Second Edition (1989) Sinauer Associates, Inc., Sunderland, Mass. (hereinafter "Brock"), or Deshpande, Mukund V., Appl. Biochem. Biotechnol., 36:227 (1992) (hereinafter "Deshpande").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element).

Biocatalytic Conversion of Phytate to Phosphate and Myo-Inositol

An aqueous reaction mixture containing the phytate is prepared by mixing the myo-inositol hexakisphosphate with an aqueous suspension of the appropriate phytase enzyme. The specific activity of the phytase enzyme (U/milligram enzyme, "U/mg") is determined by measuring the rate of conversion of a 5.0 mmol/L solution of a phytate substrate (sodium phytate) to the desired phosphate and myo-inositol product. Determination of phytase activity is based on the colorimetrical quantification at 700 nm of free phosphorus released by the hydrolysis of phytate using ammonium molybdate as color reagent. An U is the amount of phytase that liberates 1 μmol inorganic orthophosphate per minute under test conditions (pH 5.0; temperature 37° C.; and substrate concentration, sodium phytate at 0.005 mol/L).

The temperature of the hydrolysis reaction is chosen to optimize both the reaction rate and the stability of phytase. The temperature of the reaction may range from just above the freezing point of the reaction mixture (ca. 0) to 65, with a preferred range of reaction temperature of from 5 to 45. An phytase solution may be prepared by suspending the phytase in distilled water, or in an aqueous reaction mixture of a buffer that will maintain the initial pH of the reaction between 5.0 and 10.0, preferably between 6.0 and 8.0, or by suspending the immobilized phytase in a similar mixture, or by preparing a solution of a cell extract, partially purified or purified phytase(s), or a soluble form of the supernatant of cell culture in a similar mixture. After the substrata is added and as the reaction proceeds, the pH of the reaction mixture may change due to the formation of product. The reaction can be run to completely convert the phytate with no pH control, or a suitable acid or base can be added over the course of the reaction to maintain the desired pH.

EXAMPLES

The present invention is further described in the following Examples that indicate preferred embodiments of the invention. From the above discussion and these Examples, one skilled in the art can ascertain the essential characteristics of this invention, and without departing from the spirit and scope thereof, make adaptive changes and modifications for it to various uses and conditions.

General Methods

Standard method for phytase activity assay was used for thermotolerant phytase screening from different *Escherichia coli* cell strains. *Escherichia coli* cell strains were grown in LB media at 37° C. with shaking for 16 hours. Cells were broken by using French press and then suspended in buffers for phytase activity assay under designed conditions.

The other way for thermotolerant phytase screening is to identify the nova phytase genes by genomic DNA sequencing technique using the designed sequencing primers according to the phytase gene sequences in database.

Standard recombinant DNA and molecular cloning techniques used in the Examples are well known in the art. For example, pertinent specification on the operations and conditions can be found in Handbook of Molecular Cloning 3 (Joseph Sambrook & David W. Russell, Cold Spring Harbor Laboratory).

Materials and methods suitable for the maintenance and growth of bacterial cultures are well known in the art. Techniques suitable for use in the following examples may be found as set out in Manual of Methods for General Bacteriology (Phillip Gerhardt, R. G. E. Murray, Ralph N. Costilow, Eugene W. Nester, Willis A. Wood, Noel R. Krieg and G. Briggs Phillips, eds., American Society for Microbiology, Washington, D.C. (1994)) or in Brock.

The following abbreviations in the specification correspond to units of measure, techniques, properties, or compounds as follows: "sec" means second(s), "min" means minute(s), "h" means hour(s), "d" means day(s), "mL" means milliliters, "L" means liters, "mM" means millimolar, "M" means molar, "mmol" means millimole(s), "rpm" means revolutions per minute, "slpm" means standard liters per minute, "psig" means pounds per square inch, and "wt" means weight. "HPLC" means high performance liquid chromatography, "ca" means approximately, "O.D." means optical density at a specific wavelength, "dcw" means dry cell weight, and "IU" means International Units.

Example 1

Cloning of Non-K12 *Escherichia coli* Phytase

*Escherichia coli* (ATCC 9637, purchased from ATCC) was grown in a LB medium (LB Nutrient, Beijing Luqiao Technology Co. Ltd.) at 37° C. with shaking overnight. Genomic DNA was prepared using a Puregene DNA Isolation Kit according to the manufacturer's specification (Gentra Systems, Minneapolis, Minn.). PCR primers (OLIGO ID NOs.: 1~6, FIG. 3) were designed and synthesized (Invitrogen Biotechnology Co., Ltd) for cloning the genomic sequence of non-K12 *Escherichia coli* phytase. A PCR reaction was run using InsT/Aclone™ PCR Product Cloning Kit (Fermentas Life Sciences) to obtain the genomic sequence. PCR reaction mixture: 0.1 mM dNTP, 0.05 mM Primer, 10 ng genomic template DNA, 2 units Taq DNA polymerase, 5 mM $MgCl_2$, 10 mM Tris-HCl buffer pH 7.5 to a total liquid volume of 0.1 ml. The above reaction (0.1 ml) was mixed in a reaction tube (0.2 ml) and set in the DNA Thermal Cycler (Perkin-Elmer Thermocycler Type 2400) to be subjected to PCR with the following temperature conditions: 95° C. for 3 min, followed by 35 cycles of 1 min at 94° C., 1 min at 58° C., 1 min at 72° C., then 1 cycle of 7 min at 94° C.

Tow oligomers (synthesized by Invitrogen Biotechnology Co., Ltd) were used to amplify the Non-K12 phytase coding sequence from the obtained genomic DNA of *Escherichia coil* strain ATCC 9637 by PCR. The 5' primer encoded the N-terminal of the mature peptide, MQSEPELKL, and included the ribosome binding site and the restriction site NcoI (OLIGO ID NO. 7, FIG. 3). The 3' primer encoded the C-terminal of the phytase peptide, IPACSL, and included the stop codon TAA and the restriction site SnaBI (OLIGO ID NO. 8, FIG. 3). The amplified product was identified on 1.0% agarose gel electrophoresis as a DNA fragment of 1.4 kb. The fragment was isolated and purified using the DNA gel purification system (Qiagen Biochemical Co.). The purified PCR product was digested by NcoI/SnaBI (Fermentas Life Sciences) and ligated into plasmid pTrcHis2 (Invitrogen Biotechnology Co., Ltd) to obtain the recombinant plasmid pTrcHis2-PhE (see FIG. 5). Sequencing of the obtained plasmid pTrcHis2-PhE showed correct insertion of an insert having the sequence as set forth in SEQ ID NO: 1 excluding the sequence for the signal peptide.

1 microliter of ligation reaction was mixed with 50 microliters of electrocompetent *E. coli* MG1655 cells (ATCC 700926, purchased from ATCC). The mixture was subjected to a high voltage pulse (Bio-Rad electroporation system). The reaction was then incubated in 0.45 ml a SOC medium (0.5% yeast extract, 2.0% tryptone, 10 mM NaCl, 2.5 mM KCl, 10 mM $MgCl_2$, 10 mM $MgSO_4$ and 20, mM glucose) at 37° C. with shaking for 1 hour. The culture was then spread on LB agar plates containing 100 mg/ml ampicillin sulfate for growth overnight. Transformed colonies (pTrcHis2-PhE/MG1655) were then selected and used for phytase gene expression.

Example 2

Expression of Non-K12 *Escherichia coli* Phytase (W-PhE) in *Escherichia coli*

The *E. coli* transformant obtained in Example 1 was cultured with shaking for 20 hours at 37° C. in a culture medium (1% tryptone, 0.5% yeast extract, 1% sodium chloride, 50 μg/ml ampicillin). The overnight culture was added, at a ratio of 1/100 volume, into a fresh medium the same as the above, and was incubated under the same condition. When the culture reached $OD_{550}$ 0.5, 1 M IPTG was added to a final concentration of 1 mM. The incubation was continued for another 20 hours to induce the phytase gene expression. The cells were harvested by centrifugation, washed twice with distilled water, and then suspended at 100 mg wet cells/ml in HAC-Na buffer (0.1 M, pH 5.8). The harvested cells were then disrupted using an ultrasonic disintegrator (COSMO BIO CO., LTD). The supernatant was separated from the debris and subjected to SDS-polyacrylamide gel electrophoresis. The expressed protein was confirmed by the electrophoresis, which showed the existence of a protein having a molecular weight of 47 kD as expected. Further, N-terminal sequencing of the protein purified as described in Example 7 below by Edman degradation indicated a correct amino acid sequence as set forth in SEQ ID NO: 3.

Phytase activity of the harvested cells was assayed. The harvested cells (50 mg/mL), sodium phytate (0.3 M) and buffer (0.1 M HAC-Na, pH 5.8), was mixed at ambient temperature. The phytate conversion was detected in the HPLC assay as previously taught (Chen Q C, Li B W (2003) Separation of phytic acid and other related inositol phosphates by high-performance ion chromatography and its applications. *J Chromatogr A* 1018: 41-52).

Example 3

Production of Non-K12 *Escherichia coli* Phytase (W-PhE) Via Fermentation of *Escherichia coli*

The production of non-K12 *E. coli* phytase in a 14 L Braun Biostat C fermentor (B. Braun Biotech International Gmbh, Melsungen, Germany) used the mineral medium containing glucose, ammonia, and yeast extract (OXOID LTD., BASINFSTOKE HAMPSHIRE, ENGLAND).

*E. coli* strain pTrcHis2-PhE/MG1655 harboring plasmid pTrcHis2-PhE prepared in Example 1 was grown in a LB medium to prepare the seed culture for inoculation. The 500 mL seed culture was grown in a 2 L flask at 37° C., 300 rpm until OD ($\lambda$=550)>2.0. This may take about 10 hrs.

The vessel medium was prepared in an initial batch volume of 7.5 L, which contained 32 g $KH_2PO_4$, 8.0 g $MgSO_4.7H_2O$, 8.0 g $(NH_4)_2SO_4$, 50 g yeast extract, and 10 mL Mazu DF204 antifoam (BASF Corporation, Mount Olive, N.J.) in distilled water. The fermentor filled with the medium was then steam sterilized. Following sterilization, 369 g glucose aqueous solution (60% w/w), 160 mL trace element solution (Table 1), and 100 mg/L ampicillin were added. $NH_4OH$ (40% w/v) and 20% w/v $H_2SO_4$ were used to adjust pH to 6.8.

TABLE 1

Trace element solution

| Trace Element | Concentration (g/L) | Trace Element | Concentration (g/L) |
|---|---|---|---|
| $MnSO_4 \cdot 5H_2O$ | 0.001 | $H_3BO_4$ | 0.0005 |
| $CoCl_2 \cdot 6H_2O$ | 0.004 | $FeSO_4 \cdot 7H_2O$ | 0.02 |
| $Na_2MoO_4 \cdot 2H_2O$ | 0.002 | $CaCl_2 \cdot 2H_2O$ | 0.02 |
| $ZnCl_2$ | 0.002 | $MgSO_4 \cdot 7H_2O$ | 0.3 |
| $CuSO_4 \cdot 5H_2O$ | 0.001 | | |

The seed culture was added into the fermentor filled with the initial batch Vessel medium prepared above at the ratio of 5%(v/v).

The control of agitation, aeration, pH, pressure, dissolved oxygen concentration (DO), and temperature were as described in Table 2 below. The dissolved oxygen concentration was controlled at 25% of air saturation by adjusting the agitation and aeration according to the change in oxygen demand. Glucose feed was started at <5 g/L at time 0, and the feeding rate was well controlled to have the specific cell growth rate controlled at about 10-35% per hour. Glucose feed rate was reduced if glucose accumulated above 2 g/L.

TABLE 2

Several settings of fermentation

| agitation | 200 rpm | pressure | 1 atm |
|---|---|---|---|
| aeration | 0.4 L/min | dissolved oxygen concentration (DO) | 85-90% |
| pH | 6.8 | temperature | 37° C. |

When the culture densities in the fermentor reached at OD. ($\lambda$=550) of 20-30, an additional aliquot of ampicillin was added to a final concentration of 100 mg/L. When the culture densities reached OD. ($\lambda$=550) of 30-35, IPTG was added to 1 mM.

About five hours after the IPTG addition, the broth was chilled to 5-10° C. and discharged. The cells were harvested by centrifugation at 25000 g, 10° C., 10 mins. 490 g of wet cells was harvested.

The harvested cells were then disrupted using an ultrasonic disintegrator (COSMO BIO CO., LTD). The supernatant was separated from the debris and subjected to SDS-polyacrylamide gel electrophoresis. The electrophoresis showed the existence of the protein having a molecular weight of 47 kD as expected.

Example 4

Codon Optimization for Yeast Expression Systems

The Non-K12 phytase amino acid sequence (as shown in FIG. 2, SEQ ID NO: 3) was back-translated using the preferred codons in yeast systems (NCBI database). Codons with low usage percentage (<10%) were replaced by the codons used with higher frequency. The designed coding sequence was as shown in FIG. 2 (SEQ ID NO: 2), and was synthesized by Invitrogen Biotechnology Co.

Example 5

Construction of Phytase Gene Expression Strains of Yeasts

Construction of a Phytase Gene Expression Strain of *Pichia Pastoris* (S-Ph/Pp)

Two restriction sites, EcoRI and NotI, were respectively added at the 5' and the 3' ends of the synthetic sequence prepared in Example 4 using the synthetic primers of OLIGO ID NOs: 9 and 10 (FIG. 3). The obtained sequence was digested with the EcoRI and NotI enzymes, and then ligated into pPIC9K (Invitrogen Biotechnology Co., Ltd). The obtained plasmid was transformed into *Escherichia coli* strain (*Escherichia coli* strain MG1655, ATCC 700926, purchased from ATCC) for DNA amplification. The transformed *E. coli* cell colonies were selected by culturing in a LB medium containing 50 mg/L ampicillin overnight. The recombinant plasmid DNA was prepared from the cell culture using Mini spin DNA preparation kit (Qiagen Biochemical Co.). Sequencing showed correct insertion.

The recombinant plasmid prepared above (pPIC9K-PhE, FIG. 5) was digested by BglII and transformed into *P. pastoris* strain SMD1168 (Invitrogen Biotechnology Co., Ltd) via electroporation. Transformants (S-Ph/Pp) with multiple-copy inserts of phytase gene expression cassette was screened via G418 resistant selection as previously taught (Scorer, C. A., Clare, J. J., McCombie, W. R., Romanos, M. A. and Sreekrishna, K. (1994) Rapid selection using G418 of high copy number transformants of *Pichia pastoris* for high-level foreign gene expression. Biotechnology 12, 181-184).

Construction of a Phytase Gene Expression Strain of *Pichia Methanolica* (S-Ph/Pm)

The strain was constructed substantially in the same way as the above. Two restriction sites, PstI and NotI, were respectively added at the 5' and the 3' ends of the synthetic sequence prepared in Example 4 using the synthetic primers of OLIGO ID NO: 11 and 12 (FIG. 3). The obtained sequence was digested with the PstI and NotI enzymes, and then ligated into plasmid pMETalphaA (Novagen, Inc.). The obtained plasmid was amplified in *Escherichia coli* strain MG1655 and recovered as said above. Sequencing showed correct insertion.

The recombinant plasmid prepared above (pMET-PhE, FIG. 5) was digested by AscI and transformed into *Pichia methanolica* PMD16 (Novagen, Inc.) via electroporation. Transformants (S-Ph/Pm) were selected as said above.

Construction of a Phytase Gene Expression Strain of *Kluyeromyces lactis* (S-Ph/Kill)

The strain was constructed substantially in the same way as the above. Two restriction sites, BglII and StuI, were respectively added at the 5' and the 3' ends of the synthetic sequence prepared in Example 4 using the synthetic primers of OLIGO ID NO: 13 and 14 (FIG. 3). The obtained sequence was digested with the BglII and StuI enzymes, and then ligated into plasmid pKLAC1 (New England Biolabs, Inc.). The obtained plasmid was amplified in *Escherichia coli* strain MG1655 and recovered as said above. Sequencing showed correct insertion.

The recombinant plasmid prepared above (pKLAC-PhE, FIG. 5) was digested by SacII and transformed into *Kluyeromyces lactis* GG799 (New England Biolabs, Inc.) via electroporation. Transformants (S-Ph/Kill) were selected as said above.

Example 6

Fermentation of *P. pastoris* Strain (S-Ph/Pp)

This example demonstrated a process of high density fermentation of the transformed *Pichia pastoris* (S-Ph/Pp) of the invention in a 5 liter fermentor (Gaoji biotech Co. Ltd., Shanghai, China). The fermentation process included three major stages.

In stage I (Cell growth stage), 200 mL of a culture of *P. pastoris* (S-Ph/Pp, prepared in Example 5) in a YPD medium (Glucose 2%, peptone 1%, Yeast Extract 0.5%, grown at 30° C. until $OD_{550}$ 0.3~0.4, about 20 hrs) was inoculated (5 v/v %) into a Basal salts medium (2000 ml) (phosphoric acid 26.7 ml/L, calcium sulfate 0.93 g/L, potassium sulfate 18.2 g/L, Magnesium Sulfate 14.9 g/L, potassium hydrate 4.13 g/L, Glucose 40 g/L), which had been adjusted to pH 5.0 prior to inoculation using 28% $NH_3 \cdot H_2O$. PTM1 (Cupric sulfate 24 mM, Sodium iodide 0.534 mM, Manganese sulfate 17.8 mM, Sodium molybdate 0.827 mM, boric acid 0.323 mM, Cobalt chloride 2.1 mM, zinc chloride 0.147 mM, ferrous sulfate 0.234 mM, biotin 1.64 mM, sulfuric acid 0.188 M) was added to the medium at the volume ratio of 4.37 mL/L medium. The culturing was run with agitation and aeration for about 18-24 hrs, The dissolved oxygen reduced to below 100% due to the growth of cells, and increased to above 80% when the carbon resource was exhausted. At that time, the density of cells reached 90~110 g/L (wet weight).

In stage II (carbon feeding stage), a solution of 25% (w/v) glucose and 12 mL/L PTM1 in distilled water was added at the rate of 28 mL/h over 4 h. The dissolved oxygen was maintained above 20% by adjusting the aeration. At the end of this stage, the density of cells reached 180~220 g/L (wet weight).

Finally, in stage III (induction stage), 12 mL/L PTM1 in methanol was added at the rate of 20~40 ml/h. The concentration of methanol was kept not more than 0.3% (v/v), and the dissolved oxygen was maintained above 20%. Samples of the culture were collected every ~10 hrs during the induction stage for enzymatic activity analysis and SDS-PAGE (see FIG. 9).

The cell density reached an $OD_{600}$ of about 150 at 194th hour, and the phytase activity reached 4,770 U/mL at 209th hour (See FIG. 8).

The culture samples were centrifuged at 25,000 g for 10 min. The obtained supernatants were run on SDS-PAGE and analyzed for protein concentration. The protein concentration was measured by Folin-phenol method as previously described (Lowry O H et al. PROTEIN MEASUREMENT WITH THE FOLIN PHENOL REAGENT. J Biol Chem. 1951, 193 (1):265-75). The protein concentration of the final sample at about 198th hour reached 2.7 g/L. The end point and discharge time were determined by monitoring the growth and production rates as commonly known and practiced in the art.

As shown in FIG. 9, the richest band on the SDS-PAGE (12% gel) was identified via phytase activity assay (see example 7) to be the expressed phytase secreted into the culture. The concentration of the expressed phytase increased with the progress of the fermentation. The protein had a molecular weight of around 52 kDa.

Example 7

Purification of the Expressed Phytase

All the following operations were carried out at 4° C. The Non-K12 phytase was expressed in *Pichia pastoris* (Example 6). The culture was then centrifuged at 25,000 g for 10 min. The supernatant was mixed with 75% saturated ammonium sulfate under agitation for 2 hrs, and the mixture was centrifuged at 25,000 g for 15 mins. The pellet was then resuspended in 20 ml 20 mM acetate buffer, pH 5.0, and dialyzed overnight against the same buffer.

The dialysate was loaded onto a CM-Sephadex C-50 column (Pharmacia) equilibrated with 20 mM acetate buffer, pH 5.0. After the column was washed with the same buffer to remove unbound compounds, the bound phytase was eluted with a linear gradient of 0-500 mM NaCl in the starting buffer (pH 5.0 20 mM HAC-NaAC buffer).

The fractions exhibiting the highest phytase activity (see below) were pooled and dialyzed against deionized water overnight. The dialysate was used in the following studies.

Sequencing of the purified protein indicated a correct amino acid sequence as set forth in SEQ ID NO: 3.

Example 8

Characterization of the Non-K12 Phytase Activity

Determination of Phytase Activity

The protein concentration of phytase was measured as previously described (Lowry O H et al. PROTEIN MEA- SUREMENT WITH THE FOLIN PHENOL REAGENT. J Biol Chem. 1951, 193 (1):265-75).

Determination of the phytase activity is based on the colorimetrical quantification at 700 nm of free phosphorus released by the hydrolysis of phytate using ammonium molybdate as the color reagent. One "U" is the amount of enzyme that liberates 1 μmol inorganic orthophosphate per minute under standard assay conditions (pH 5.0; temperature 37° C.; and substrate concentration, sodium phytate at 0.005 mol/L; also see GB/T18634-2002, and Study On The Determination Condition Of Phytase Activity By Molybdenum Yellow And Molybdenum Blue Method, Zou DaQiong. CHINA FEED, 2005 (03)).

The specific enzyme activity was calculated by the following formula:

$$Uc=U/C$$

Uc—phytase specific activity, U/mg;
U—phytase activity, U/ml;
C—the protein concentration of phytase, mg/ml The specific activity of the phytase from Example 6 purified above was measured to be 3146 U/mg

Optimum pH and Temperature

The phytase activity was measured at different pH under standard assay conditions (see above), using pH 3.0~6.0 in a 0.05 mol/L sodium acetate/acetic acid buffer and pH 6.0~9.0 in a 0.04 mol/L Barbital Sodium-HCl buffer. The phytase activity was measured at different temperatures under standard assay conditions (see above). The measurements were carried out with the purified phytase in Example 7. The results were shown in FIGS. 6 and 7.

The optimum pH of the purified phytase was 3 to 6 (See FIG. 6). The optimum temperature of the purified phytase was around 55° C. (See FIG. 7).

Effects of pH and Temperature on the Expressed Phytase

The Non-K12 phytase purified in Example 7 was diluted in buffers with varying pH values (pH 3.0~6.0, 0.05 mol/L HAC/NaAC buffer and pH 6.0~9.0, 0.04 mol/L Barbital Sodium-HCl buffer) to a final concentration of 1.5 mg/ml, and incubated in 37° C. for 1 hr. The phytase was diluted in a 0.05 mol/L HAC-NaAC buffer at pH 5.0 and incubated at different temperatures for 1 h. The phytase activity was measured under standard assay conditions (see above). The results were shown in FIGS. 12 and 13.

As shown in FIG. 12, the Non-k12 phytase of the invention was stable against low pH of 2-5.5 (as shown in FIG. 12). The thermo-stability of the Non-k12 phytase of the invention was shown in FIG. 13, at least 17% activity was maintained at a temperature up to 80° C. after 1 hr, at least 33% activity at a temperature up to 90° C. after 1 hr, and at least 26% activity at a temperature up to 100° C. after 1 hr (FIG. 13).

Phytase Resistance to Pepsin and Pancreatic Protease

The Non-k12 phytase of the invention purified in Example 7 was incubated with pepsin (300 U/ml, pH 2.5, 37° C., 2 hs) and pancreatic protease (30 U/ml, at pH 7.0, 37° C., 2 hs), respectively. In either treatment, at least 91% activity of the purified Non-K12 phytase was maintained (as showed in FIG. 10). The control (100% activity) was a parallel incubation without the protease treatment.

Size of the Expressed Phytase

The SDS-PAGE (12% gel) indicated that the phytase expressed in P. pastoris (Example 6) showed a molecular weight around 52 kDa. The expressed phytase in P. pastoris was believed to be partially glycosylated, as shown by the blurred band on SDS-PAGE (as shown in FIG. 11).

Effects of Temperature on the Dried Phytase Formulation

The Non-K12 phytase purified in Example 7 was formulated (25% starch, 12.5% dextrin, 5% sodium chloride, 5% potassium sorbate, 1.5% calcium sulfite (w/w)), and spray-dried. The dried phytase formulation was incubated at different temperatures for 1 hr. The phytase activity was measured under standard assay conditions (see above).

The thermo-stability of formulated lyophilized phytase was shown in FIG. 14, 70% activity remained even at a temperature as high as 100° C. after 1 hr.

Example 9

Comparison of Non-K12 Phytase with E. Coli K12 Phytase and the Fungal Phytase from Aspergillus niger The fungal phytase from Aspergillus niger (Robert F. M. Van Gorcom et al. Cloning and expression of phytase from aspergillus. U.S. Pat. No. 5,436,156) and E. coli K12 phytase (Jay M. Short et al. Recombinant bacterial phytases and uses thereof. U.S. Pat. No. 6,855,365) were tested on their stability under varying pH values and temperatures as above (Example 8, "Effects of pH and temperature on the expressed phytase"). The obtained results were compared with those obtained with the Non-K12 phytase of the invention prepared in Example 6 and purified as in example 7. The comparisons were shown in FIGS. 15 and 16. As indicated, the Non-K12 phytase of the invention was significantly more thermostable (FIG. 15) and more tolerant to acid environment (FIG. 16).

The invention claimed is:

1. An isolated cDNA comprising a nucleotide sequence selected from the group consisting of:
   a) a nucleotide sequence encoding a polypeptide comprising the amino acid sequence of SEQ ID NO: 3; and
   b) the nucleotide sequence completely complementary to a).

2. An isolated nucleic acid molecule comprising a nucleotide sequence encoding a polypeptide comprising the amino acid sequence of SEQ ID NO: 3, wherein the nucleotide sequence is selected from the group consisting of:
   a) the nucleotide sequence consisting of nucleotides 67-1296 of SEQ ID NO: 1;
   b) the nucleotide sequence consisting of nucleotides 1-1230 of SEQ ID NO: 2; and
   c) the nucleotide sequence completely complementary to a) or b).

3. An expression vector, comprising a nucleotide sequence selected from the group consisting of:
   a) a nucleotide sequence encoding a polypeptide having the amino acid sequence of SEQ ID NO: 3; and
   b) the nucleotide sequence completely complementary to a).

4. The vector according to claim 3, wherein said vector is selected from the group consisting of pTrcHis2-PhE, pPIC9K-PhE, pMET-PhE and pKLAC-PhE.

5. An isolated cell comprising an expression vector comprising an isolated nucleic acid molecule comprising a nucleotide sequence selected from the group consisting of:
   a) a nucleotide sequence encoding a polypeptide having the amino acid sequence of SEQ ID NO: 3; and
   b) the nucleotide sequence completely complementary to a).

6. The cell according to claim 5, wherein said cell is a yeast cell.

7. The cell according to claim 5, wherein the cell is of the species selected from the group consisting of *Escherichia coli, Pichia pastoris, Pichia methanolica* and *Kluyeromyces lactis*.

8. The cell according to claim 5, wherein the cell is derived from a strain selected from the group consisting of *E. coli* MG1655, *P. pastoris* GS115, *P. methanolica* PMAD16 and *Kluyeromyces lactis* GG799.

9. The cell according to claim 5, wherein the cell is a strain selected from the group consisting of *E. coli* MG1655 transformed with pTrcHis2-PhE, *P. pastoris* SMD1168 transformed by pPIC9K-PhE, *P. methanolica* PMD16 transformed by pMET-PhE and *Kluyeromyces lactis* GG799 transformed by pKLAC-PhE.

10. An isolated polypeptide comprising the amino acid sequence of SEQ ID NO: 3, and having phytase activity.

11. A process for production of a Non-K12 *Escherichia coli* phytase by fermentation, comprising a step of cultivating a cell according to claim 5, that is a strain selected from the group consisting of *E. coli* MG1655 transformed with pTrcHis2-PhE, *P. pastoris* SMD1168 transformed by pPIC9K-PhE, *P. methanolica* PMD16 transformed by pMET-PhE and *Kluyeromyces lactis* GG799 transformed by pKLAC-PhE, under a condition effective for expression to obtain a polypeptide having phytase activity.

* * * * *

SEQUENCE LISTING

<160> NUMBER OF SEQ ID NOS: 6

<210> SEQ ID NO 1
<211> LENGTH: 1299
<212> TYPE: DNA
<213> ORGANISM: Escherichia coli

<400> SEQUENCE: 1
atgaaagcga tcttaatccc attttatct cttctgattc cgttaacccc gcaatctgca        60

```
ttcgctcaga gtgagccgga gctgaagctg gaaagtgtgg tgattgtcag tcgtcatggt    120
gtgcgtgctc caaccaaggc cacgcaactg atgcagggtg tcaccccaga cgcatggcca    180
acctggccgg taaaactggg ttggctgaca ccgcgcggtg gtgagctaat cgcctatctc    240
ggacattacc aacgccagcg tctggtagcc gacggattgc tggcgaaaaa gggctgcccg    300
cagtctggtc aggtcgcgat tattgctgat gtcgacgagc gtacccgtaa aacaggcgaa    360
gccttcgccg ccgggctggc acctgactgt gcaataaccg tacataccca ggcagatacg    420
tccagtcccg atccgttatt taatcctcta aaaactggcg tttgccaact ggataactcg    480
aacgtgactg acgcgatcct cagcagggca ggagggtcaa ttgctggctt taccgggcat    540
cggcaaacgg cgtttcgcga actggaacgg gtgcttaatt ttccgcaatc aaacttgtgc    600
cttaaacgtg agaaacagga cgaaagctgt tcattaacgc aggcattacc atcggaactc    660
aaggtgagcg ccgacaatgt ctcattaacc ggtgcggtaa gcctcgcatc aatgctgacg    720
gagatatttc tcctgcaaca agcacaggga atgccggagc cggggtgggg aaggatcacc    780
gattcacacc agtggaacac cttgctaagt ttgcataacg cgcaatttta tttgttacaa    840
cgcacgccag aggttgcccg cagccgcgcc accccgttat tagatttgat caagacagcg    900
ttgacgcccc atccaccgca aaaacaggcg tatggtgtga cattacccac ttcagtgctg    960
tttatcgccg gacacgatac taatctggca aatctcggcg gcgcactgga gctcaactgg   1020
acgcttcccg gtcagccgga taacacgccg ccaggtggtg aactggtgtt tgaacgctgg   1080
cgtcggctaa gcgataacag ccagtggatt caggtttcgc tggtcttcca gactttacag   1140
cagatgcgtg ataaaacgcc gctgtcatta aatacgccgc ccggagaggt gaaactgacc   1200
ctggcaggat gtgaagagcg aaatgcgcag ggcatgtgtt cgttggcagg ttttacgcaa   1260
atcgtgaatg aagcacgcat accggcgtgc agtttgtaa                          1299
```

```

<210> SEQ ID NO 2
<211> LENGTH: 1233
<212> TYPE: DNA
<213> ORGANISM: Artificial Sequence
<220> FEATURE:
<221> NAME/KEY: CDS
<222> LOCATION: (1)..(1230)
<223> OTHER INFORMATION: modified DNA sequence of E. Coli non-K12
      phytase

<400> SEQUENCE: 2
caa tcc gaa cca gag ttg aag ctc gaa tcc gtc gtg atc gtt tcc aga       48
Gln Ser Glu Pro Glu Leu Lys Leu Glu Ser Val Val Ile Val Ser Arg
1               5                   10                  15
cac ggt gtt aga gcc cca act aaa gct act caa ttg atg caa ggt gtc       96
His Gly Val Arg Ala Pro Thr Lys Ala Thr Gln Leu Met Gln Gly Val
            20                  25                  30
act cct gac gct tgg cca act tgg cca gtc aaa ttg ggt tgg ttg acc      144
Thr Pro Asp Ala Trp Pro Thr Trp Pro Val Lys Leu Gly Trp Leu Thr
        35                  40                  45
cca aga ggt ggt gaa ttg att gcc tac ttg ggt cac tac caa aga caa      192
Pro Arg Gly Gly Glu Leu Ile Ala Tyr Leu Gly His Tyr Gln Arg Gln
    50                  55                  60
aga ttg gtt gct gac ggg ttg ttg gcc aag aag ggt tgt cca caa tct      240
Arg Leu Val Ala Asp Gly Leu Leu Ala Lys Lys Gly Cys Pro Gln Ser
65                  70                  75                  80
ggt caa gtc gct att att gcc gac gtt gac gaa aga acc aga aag acc      288
Gly Gln Val Ala Ile Ile Ala Asp Val Asp Glu Arg Thr Arg Lys Thr
                85                  90                  95
```

```
                                                                           -continued
ggt gaa gct ttc gcc gcc ggt ctc gcc cca gac tgt gct atc act gtc    336
Gly Glu Ala Phe Ala Ala Gly Leu Ala Pro Asp Cys Ala Ile Thr Val
            100                 105                 110 cac acc caa gcg gac act tct tcc cca gac cca ttg ttc aac cca ttg    384
His Thr Gln Ala Asp Thr Ser Ser Pro Asp Pro Leu Phe Asn Pro Leu
        115                 120                 125 aag acc ggt gtc tgt caa ctc gac aac tct aac gtc acc gac gcc att    432
Lys Thr Gly Val Cys Gln Leu Asp Asn Ser Asn Val Thr Asp Ala Ile
130                 135                 140 ttg tcc aga gcc ggt ggt tct atc gct ggt ttc acc ggt cac aga caa    480
Leu Ser Arg Ala Gly Gly Ser Ile Ala Gly Phe Thr Gly His Arg Gln
145                 150                 155                 160 act gct ttc aga gaa ttg gag aga gtc ctc aac ttc cca caa tct aac    528
Thr Ala Phe Arg Glu Leu Glu Arg Val Leu Asn Phe Pro Gln Ser Asn
                165                 170                 175 ctc tgt ttg aag aga gag aag caa gac gaa tcc tgt tcc ttg acc caa    576
Leu Cys Leu Lys Arg Glu Lys Gln Asp Glu Ser Cys Ser Leu Thr Gln
            180                 185                 190 gcc ttg cca tct gag ttg aag gtc tct gct gac aac gtt tct ttg acc    624
Ala Leu Pro Ser Glu Leu Lys Val Ser Ala Asp Asn Val Ser Leu Thr
        195                 200                 205 ggt gcc gtc tcc ttg gct tcc atg ttg acc gag atc ttc ctc ttg caa    672
Gly Ala Val Ser Leu Ala Ser Met Leu Thr Glu Ile Phe Leu Leu Gln
210                 215                 220 caa gcc caa ggt atg cca gaa cca ggt tgg ggt aga att acc gac tcc    720
Gln Ala Gln Gly Met Pro Glu Pro Gly Trp Gly Arg Ile Thr Asp Ser
225                 230                 235                 240 cac caa tgg aac acc ttg ttg tcc ttg cac aac gct caa ttc tac ttg    768
His Gln Trp Asn Thr Leu Leu Ser Leu His Asn Ala Gln Phe Tyr Leu
                245                 250                 255 ctc caa aga acc cca gag gtc gct aga tcc aga gcc act cca ctc ttg    816
Leu Gln Arg Thr Pro Glu Val Ala Arg Ser Arg Ala Thr Pro Leu Leu
            260                 265                 270 gac ctc att aag acc gcc ttg act cca cac cca caa aag caa gct        864
Asp Leu Ile Lys Thr Ala Leu Thr Pro His Pro Gln Lys Gln Ala
        275                 280                 285 tac ggt gtt acc ttg cca acc tcc gtc ttg ttc att gcc ggt cat gac    912
Tyr Gly Val Thr Leu Pro Thr Ser Val Leu Phe Ile Ala Gly His Asp
290                 295                 300 acc aac ttg gct aac ttg ggt ggt gcc ctc gaa ctc aac tgg act ttg    960
Thr Asn Leu Ala Asn Leu Gly Gly Ala Leu Glu Leu Asn Trp Thr Leu
305                 310                 315                 320 cca ggt caa cca gac aac acc cca cca ggt ggt gaa ttg gtt ttc gaa   1008
Pro Gly Gln Pro Asp Asn Thr Pro Pro Gly Gly Glu Leu Val Phe Glu
                325                 330                 335 aga tgg aga aga ctc tcc gac aac tct caa tgg att caa gtc tct ttg   1056
Arg Trp Arg Arg Leu Ser Asp Asn Ser Gln Trp Ile Gln Val Ser Leu
            340                 345                 350 gtc ttc caa acc ttg caa caa atg aga gac aag act cca ctc tcc ttg   1104
Val Phe Gln Thr Leu Gln Gln Met Arg Asp Lys Thr Pro Leu Ser Leu
        355                 360                 365 aac acc cca cca ggt gag gtc aag ttg acc ctc gct ggt tgt gaa gaa   1152
Asn Thr Pro Pro Gly Glu Val Lys Leu Thr Leu Ala Gly Cys Glu Glu
370                 375                 380 aga aac gcc caa ggt atg tgt tct ttg gcc ggt ttc act caa atc gtt   1200
Arg Asn Ala Gln Gly Met Cys Ser Leu Ala Gly Phe Thr Gln Ile Val
385                 390                 395                 400 aac gaa gct aga atc cca gcc tgt tct ttg taa                       1233
Asn Glu Ala Arg Ile Pro Ala Cys Ser Leu
                405                 410
```

<210> SEQ ID NO 3
<211> LENGTH: 410
<212> TYPE: PRT
<213> ORGANISM: Escherichia coli

<400> SEQUENCE: 3

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Gly Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ser Asn Val Thr Asp Ala Ile
    130                 135                 140

Leu Ser Arg Ala Gly Gly Ser Ile Ala Gly Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380
```

-continued

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 432
<212> TYPE: PRT
<213> ORGANISM: Escherichia coli Non-K12

<400> SEQUENCE: 4

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Gly Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ser
145                 150                 155                 160

Asn Val Thr Asp Ala Ile Leu Ser Arg Ala Gly Gly Ser Ile Ala Gly
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 5
<211> LENGTH: 432
<212> TYPE: PRT
<213> ORGANISM: Escherichia coli K12

<400> SEQUENCE: 5

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Lys Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

```
Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
            325                 330                 335

Glu Leu Asn Trp Thr Leu Pro Gly Gln Pro Asp Asn Thr Pro Pro Gly
        340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 6
<211> LENGTH: 432
<212> TYPE: PRT
<213> ORGANISM: Pig Colon Escherichia coli

<400> SEQUENCE: 6

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Val Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Ser Gln Leu Asn Leu Cys Leu Asn Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255
```

-continued

```
Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
            275                 280                 285

Arg Ala Thr Pro Leu Leu Asp Leu Ile Met Ala Ala Leu Thr Pro His
            290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```